US008822635B2

(12) United States Patent
Sotzing et al.

(10) Patent No.: US 8,822,635 B2
(45) Date of Patent: Sep. 2, 2014

(54) SELENIUM-BASED MONOMERS AND CONJUGATED POLYMERS, METHODS OF MAKING, AND USE THEREOF

(71) Applicants: Gregory A. Sotzing, Mansfield Center, CT (US); Tanmoy Dey, Willington, CT (US)

(72) Inventors: Gregory A. Sotzing, Mansfield Center, CT (US); Tanmoy Dey, Willington, CT (US)

(73) Assignee: The University of Connecticut, Farmington, CT (US)

( * ) Notice: Subject to any disclaimer, the term of this patent is extended or adjusted under 35 U.S.C. 154(b) by 0 days.

(21) Appl. No.: 13/923,502

(22) Filed: Jun. 21, 2013

(65) Prior Publication Data

US 2013/0289286 A1 Oct. 31, 2013

Related U.S. Application Data

(62) Division of application No. 13/406,925, filed on Feb. 28, 2012, now Pat. No. 8,513,377.

(60) Provisional application No. 61/448,290, filed on Mar. 2, 2011.

(51) Int. Cl.
  *C08G 65/00* (2006.01)
(52) U.S. Cl.
  USPC .......................................... 528/406; 528/403
(58) Field of Classification Search
  USPC .................................................. 528/406, 403
  See application file for complete search history.

(56) References Cited

U.S. PATENT DOCUMENTS

| 5,111,327 | A | 5/1992 | Blohm et al. |
| 6,635,729 | B1 | 10/2003 | Groenendaal et al. |
| 6,791,738 | B2 | 9/2004 | Reynolds et al. |
| 6,995,223 | B2 | 2/2006 | Groenendaal et al. |
| 7,951,902 | B2 | 5/2011 | Sotzing |
| 2004/0072987 | A1 | 4/2004 | Groenendaal et al. |
| 2005/0157369 | A1 | 7/2005 | Xu et al. |
| 2005/0246888 | A1 | 11/2005 | Reynolds et al. |
| 2006/0262377 | A1 | 11/2006 | Kojima |
| 2007/0191576 | A1 | 8/2007 | Sotzing |
| 2009/0203873 | A1 | 8/2009 | Sotzing |
| 2010/0113727 | A1 | 5/2010 | Sotzing |
| 2010/0283040 | A1* | 11/2010 | Bendikov et al. ............... 257/40 |
| 2011/0201826 | A1 | 8/2011 | Sotzing |

FOREIGN PATENT DOCUMENTS

| WO | 03046106 A1 | 6/2003 |
| WO | 03054052 A1 | 7/2003 |
| WO | 03054053 A1 | 7/2003 |
| WO | 2004031192 A1 | 4/2004 |
| WO | 2006117800 A2 | 11/2006 |
| WO | 2007066353 A2 | 6/2007 |

OTHER PUBLICATIONS

Ozkut et al. (J. Mater. Chem., 2011, 21, 5268-5272).*
Campos et al., "Photovoltaic activity of a PolyProDOT derivative in a bulk heterojunction solar cell", Solar Energy Materials & Solar Cells 90, 2006, pp. 3531-3546.

(Continued)

*Primary Examiner* — Shane Fang
(74) *Attorney, Agent, or Firm* — Cantor Colburn LLP

(57) ABSTRACT

Substituted selenophene monomers, and polymers and copolymers having units derived from a substituted selenophene are disclosed. Also provided are methods of making and using the same.

10 Claims, 2 Drawing Sheets

(56) References Cited

OTHER PUBLICATIONS

Coffey et a., "A Facile Synthesis of 3,4-Dialkoxythiophenes", Synthetic Communications, 26(11), 1996, pp. 2205-2212.
DE10036954 A1, Feb. 21, 2002, Abstract Only, 1 Page.
Galand et al., "Spray Processable Hybrid 3,4-Propylenedioxythionphene: Phenylene Electrochromic Polymers", Macromolecules 39, 2006, pp. 7286-7294.
Gaupp et al., "Composite Coloration Efficiency Measurements of Electrochromic Polymers Based on 3,4- Alkylenedioxythiophenes", Chem. Mater. 14, 2002, pp. 3694-3970.
Gaupp et al., "Poly(ProDOT-Et2): A High-Contrast, High-Coloration Efficiency Electrochromic Polymer", Macromol. Rapid. Commun. 23, 2002, pp. 885-889.
Heywang et al., "Poly(alkylenedioxythiophene)s- New, Very Stable Conducting Polymers", Advanced Materials, 4(2), 1992, pp. 116-118.
Kumar et al., "Conducting Poly(3,4-alkylenedioxythiophene) Derivatives as Fast Electrocrhomics with High-Contrast Ratios", Chem. Mater. 10, 1998, pp. 896-902.
Padilla et al., "Electrochemical study of dual conjugated polymer electrochromic devices", Journal of Electroanalytical Chemistry, 609(2), 2007, pp. 75-84.
Padilla et al., "High contrast solid-state electrochromic devices frmo substituted 3,4-propylenedioxythiophenes using the dual conjugated polymer approach", Synthetic Metals 157, 2007, pp. 261-268.
International Search Report for International Application No. PCT/US2012/026959, International Filing Date Feb. 28, 2012, Date of Mailing Sep. 24, 2012, 5 pages.
Written Opinion of International Application No. PCT/US2012/026959, International Filing Date Feb. 28, 2012, Date of Mailing Sep. 24, 2012, 3 pages.
Reeves et al., "Dual Cathodically and Anodically Coloring Electrochromic Polymer Based on a Spiro Bipropylenedioxythionphene [(Poly(spiroBiProDOT)]", Advanced Materials, 14 (10), 2002, pp. 717-719.
Sapp et al., "High Contrast Ratio and Fast-Switching Dual polymer Electrochromic Devices", Chem. Mater. 10, 1998, pp. 2101-2108.
Thompson et al., "Soluble Narro Band Gap and Blue Propylenedioxythiophene-Cyanovinylene Polymers as Multifunctional Materials for Photovoltaic and Electrochromic Applications", J. Am. Chem. Soc. 128, 2006, pp. 12714-12725.
Walczak et al., "Easily Oxidized high Band Gap Conjugated Polymers", Polymer Preprints 45(1), 2004, p. 229.
Welsh et al., "Enhanced Contrast Ratios and Rapid Switching in Electrochromics Based on Poly(3,4-propylenedioxythiophene) Derivatives", Adv. Mater. 11(16), 1999, pp. 1379-1382.
Welsh et al., "Fast Electrochromic Polymers Based on New Poly(3,4-alkylenedioxythiophene) Derivatives", Synthetic Metals, 102, 1999, pp. 967-968.
Zong et al., "3,4-Alkylenedioxy ring formation via double Mitsunobu reactions: an efficient route for the synthesis of 3,4-ethylenedioxythiophene (EDOT) and 3,4-propylenedioxythiophene (ProDOT) derivatives as monomers for electron-rich conducting polymers", Chem. Commun. 2002, pp. 2498-2499.

\* cited by examiner

SELENIUM-BASED MONOMERS AND CONJUGATED POLYMERS, METHODS OF MAKING, AND USE THEREOF

CROSS-REFERENCE TO RELATED APPLICATIONS

This application is a divisional of U.S. Nonprovisional patent application Ser. No. 13/406,925, filed Feb. 28, 2012, which claims the benefit of U.S. Provisional Application Ser. No. 61/448,290, filed Mar. 2, 2011. These priority applications are fully incorporated herein by reference.

TECHNICAL FIELD

This invention relates to selenium-based monomers, selenium-based conjugated polymers prepared therefrom, methods of producing the monomers and conjugated polymers, and applications utilizing the conjugated polymers.

BACKGROUND

Poly-3,4-ethylenedioxythiophene ("PEDOT") prepared from 3,4-ethylenedioxythiophene ("EDOT") is a well known conducting polymer. Higher photopic contrast and a more colorless bleached state is obtained by incorporation of an additional methylene unit into the EDOT repeat unit with 3,4-propylenedioxythiophene ("PropOT"). PolyPropOT exhibits enhanced electrochromic properties over conducting polymer PEDOT. PPropOT has a $\Delta\% T$ of 66% at 2 mlax compared to the 54% transmittance change for PEDOT (Sommen, G. L. *Mini-Rev. Org. Chem.* 2005, 2, 375).

Theoretical studies and calculations indicate that selenophene based polymers should have a lower band gap ($E_g$) than corresponding polythiophenes. Due to the larger size of selenium, polyselenophenes are also expected to have some advantages over polythiophenes, such as having lower oxidation and reduction potentials, being easier to polarize, and being more suitable for interchain charge transfer (which is facilitated by the intermolecular contacts between Se atoms).

Poly(3,4-ethylenedioxyselenophene) ("PEDOS") has been synthesized (Patra, A.; Wijsboom, Y. H.; Zade, S. S.; Li, M.; Sheynin, Y.; Leitus, G.; Bendikov, M. *J. Am. Chem. Soc.* 2008. 130, 6735) and is reported to exhibit a band gap of 1.4 eV. The polymer PEDOS is highly stable in its oxidized state and has well defined spectroelectrochemistry. It also has a lower band gap than PEDOT (1.6-1.7 eV).

Selenium based conductive polymers offer several challenges. Doped polyselenophenes show significantly lower conductivities ($10^{-4}$ to $10^{-1}$ S/cm) than that of doped polythiophenes (up to $10^3$ S/cm). The lack of a well-defined electrochemical response prevents their study and application and there are synthetic challenges for the synthesis of substituted selenophene-based monomeric precursors. It is presumed that the low conductivity and poor electrochemical behavior of polyselenophenes results from their instability during oxidative polymerization.

Accordingly, there remains a need in the art for new, substituted polyselenophenes with high conductivity and well-defined electrochemistry.

BRIEF SUMMARY OF THE INVENTION

In one embodiment, a polymer comprises a unit derived from a monomer according to structure (I):

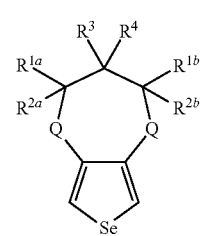

(I)

wherein each instance of Q is O or S;
each of $R^{1a}$, $R^{1b}$, $R^{2a}$, $R^{2b}$, $R^3$, and $R^4$ independently is hydrogen; $C_1$-$C_{20}$ alkyl, $C_1$-$C_{20}$ haloalkyl, aryl, $C_1$-$C_{20}$ alkoxy, $C_1$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, —$C_1$-$C_{10}$ alkyl-aryl; or hydroxyl;
with the proviso that at least one of $R^{1a}$, $R^{1b}$, $R^{2a}$, $R^{2b}$, $R^3$, and $R^4$ is not hydrogen, and when $R^{1a}$, $R^{1b}$, $R^{2a}$, and $R^{2b}$ are all hydrogen, then at least one of $R^3$ and $R^4$ is other than hydrogen, methyl, or ethyl;
wherein the $C_1$-$C_{20}$ alkyl, $C_1$-$C_{20}$ haloalkyl, aryl, $C_1$-$C_{20}$ alkoxy, $C_1$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, —$C_1$-$C_{10}$ alkyl-aryl group each may be optionally substituted with one or more of $C_1$-$C_{20}$ alkyl; aryl; halogen; hydroxyl; —N—$(R^7)_2$ wherein each $R^7$ is independently hydrogen or $C_1$-$C_6$ alkyl; cyano; nitro; —COOH; —S(=O)$C_0$-$C_{10}$ alkyl; or —S(=O)$_2$$C_0$-$C_{10}$ alkyl.

In another embodiment, a method comprises polymerizing a composition by electrochemical or chemical reaction to form a polymer, wherein the composition comprises a monomer according to the structure (I) or (Ia):

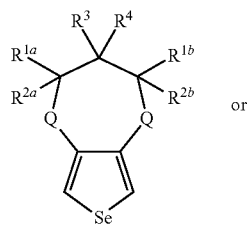

or

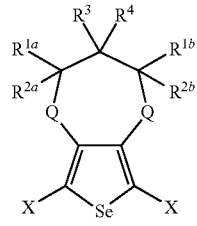

(Ia)

wherein each instance of Q is O or S;
each of $R^{1a}$, $R^{1b}$, $R^{2a}$, $R^{2b}$, $R^3$, and $R^4$ independently is hydrogen; $C_1$-$C_{20}$ alkyl, $C_1$-$C_{20}$ haloalkyl, aryl, $C_1$-$C_{20}$ alkoxy, $C_1$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, —$C_1$-$C_{10}$ alkyl-aryl; or hydroxyl;
with the proviso that at least one of $R^{1a}$, $R^{1b}$, $R^{2a}$ $R^{2b}$, $R^3$, and $R^4$ is not hydrogen, and when $R^{1a}$, $R^{1b}$, $R^{2a}$, and $R^{2b}$ are all hydrogen, then at least one of $R^3$ and $R^4$ is other than hydrogen, methyl, or ethyl;
wherein the $C_1$-$C_{20}$ alkyl, $C_1$-$C_{20}$ haloalkyl, aryl, $C_1$-$C_{20}$ alkoxy, $C_1$-$C_{20}$ haloalkoxy, aryloxy, —$C_1$-$C_{10}$ alkyl-O—$C_1$-

$C_{10}$ alkyl, —$C_1$-$C_{10}$ alkyl-O-aryl, —$C_1$-$C_{10}$ alkyl-aryl group each may be optionally substituted with one or more of $C_1$-$C_{20}$ alkyl; aryl; halogen; hydroxyl; —N—$(R^7)_2$ wherein each $R^7$ is independently hydrogen or $C_1$-$C_6$ alkyl; cyano; nitro; —COOH; —S(=O)$C_0$-$C_{10}$ alkyl; or —S(=O)$_2C_0$-$C_{10}$ alkyl; and X is chloro, bromo, or iodo.

In yet another embodiment, a compound comprises a monomer according to any one of structure (I), (Ia), (II), and (IIa):

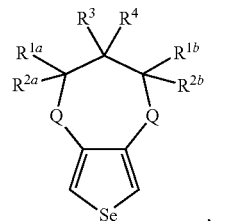
(I)

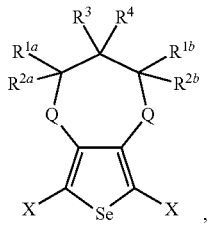
(Ia)

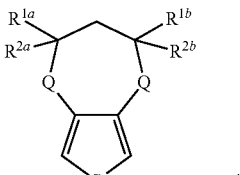
, and
(II)

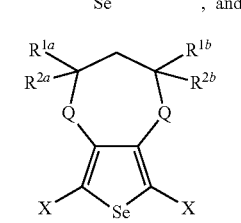
(IIa)

wherein each instance of Q is O or S;

X is chloro, bromo, or iodo;

each of $R^{1a}$, $R^{1b}$, $R^{2b}$, $R^3$, and $R^4$ independently is hydrogen; $C_1$-$C_{20}$ alkyl, $C_1$-$C_{20}$ haloalkyl, aryl, $C_1$-$C_{20}$ alkoxy, $C_1$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, —$C_1$-$C_{10}$ alkyl-aryl; or hydroxyl;

with the proviso that at least one of $R^{1a}$, $R^{1b}$, $R^{2a}$ $R^{2b}$, $R^3$, and $R^4$ is not hydrogen, and when $R^{1a}$, $R^{1b}$, $R^{2a}$, and $R^{2b}$ are all hydrogen, then at least one of $R^3$ and $R^4$ is other than hydrogen, methyl, or ethyl;

wherein the $C_1$-$C_{20}$ alkyl, $C_1$-$C_{20}$ haloalkyl, aryl, $C_1$-$C_{20}$ alkoxy, $C_1$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, —$C_1$-$C_{10}$ alkyl-aryl group each may be optionally substituted with one or more of $C_1$-$C_{20}$ alkyl; aryl; halogen; hydroxyl; —N—$(R^7)_2$ wherein each $R^7$ is independently hydrogen or $C_1$-$C_6$ alkyl; cyano; nitro; —COOH; —S(=O)$C_0$-$C_{10}$ alkyl; or —S(=O)$_2C_0$-$C_{10}$ alkyl.

In still yet another embodiment, a method of preparing a compound according to the structure (I):

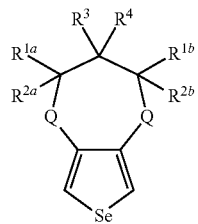
(I)

wherein each instance of Q is O;

each of $R^{1a}$, $R^{1b}$, $R^{2a}$, $R^{2b}$, $R^3$, and $R^4$ independently is hydrogen; $C_1$-$C_{20}$ alkyl, $C_1$-$C_{20}$ haloalkyl, aryl, $C_1$-$C_{20}$ alkoxy, $C_1$-$C_{20}$ haloalkoxy, aryloxy, —$C_1$-$C_{10}$alkyl-O—$C_1$-$C_{10}$ alkyl, —$C_1$-$C_{10}$ alkyl-O-aryl, —$C_1$-$C_{10}$ alkyl-aryl; or hydroxyl;

with the proviso that at least one of $R^{1a}$, $R^{1b}$, $R^{2a}$, and $R^{2b}$ is not hydrogen;

wherein the $C_1$-$C_{20}$ alkyl, $C_1$-$C_{20}$ haloalkyl, aryl, $C_1$-$C_{20}$ alkoxy, $C_1$-$C_{20}$ haloalkoxy, aryloxy, —$C_1$-$C_{10}$alkyl-O—$C_1$-$C_{10}$ alkyl, —$C_1$-$C_{10}$alkyl-O-aryl, —$C_1$-$C_{10}$alkyl-aryl group each may be optionally substituted with one or more of $C_1$-$C_{20}$ alkyl; aryl; halogen; hydroxyl; —N—$(R^7)_2$ wherein each $R^7$ is independently hydrogen or $C_1$-$C_6$ alkyl; cyano; nitro; —COOH; —S(=O)$C_0$-$C_{10}$ alkyl; or —S(=O)$_2C_0$-$C_{10}$ alkyl, comprises reacting a 3,4-dialkoxyselenophene with a substituted diol.

Other embodiments include articles and devices prepared from the polymers disclosed herein.

DETAILED DESCRIPTION OF THE INVENTION

Figure 1:
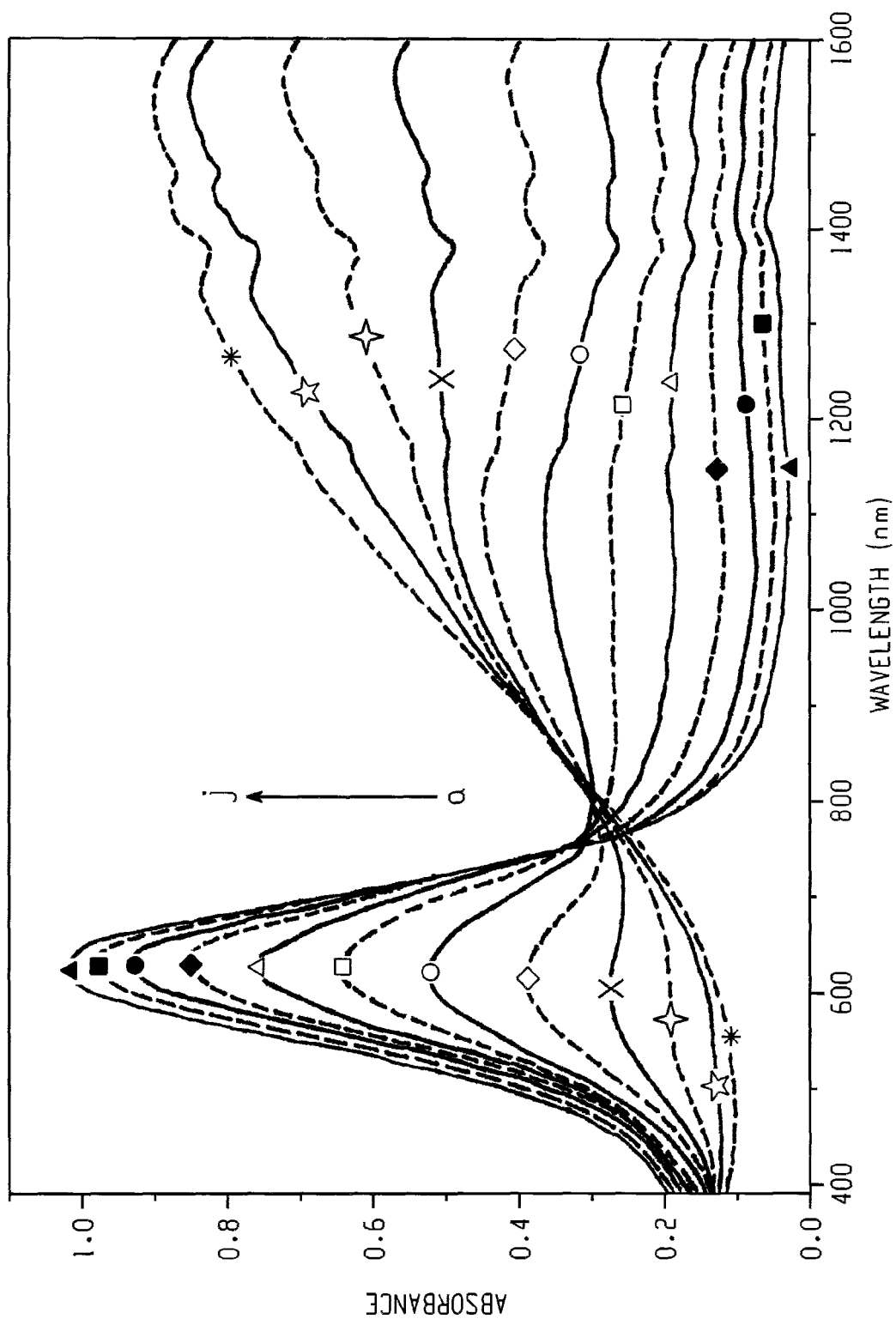
FIG. 1 illustrates the in-situ spectroelectrochemistry of PProDOS-Me$_2$ deposited onto ITO-coated-glass in 0.1 M TBAPF$_6$/ACN.

Disclosed herein are substituted 3,4-propylenedioxyselenophene monomers ("substituted ProDOS monomers") substituted at the 1, 3 or 1 and 3 positions of the propylene moiety (i.e. alpha to the monomer oxygen(s)), and optionally further substituted at the 2 position, the central methylene unit. Also disclosed are the corresponding substituted 3,4-propylenedithioselenophene monomers ("substituted PropTS monomers"), substituted at the 1, 3 or 1 and 3 positions of the propylene moiety, and optionally further substituted at the 2 position. The substituted ProDOS monomers and substituted PropTS monomers are collectively referred to as ProDOS/DTS monomers. Upon conjugation, the resulting electrochromic conjugated polymers ("substituted ProDOS polymers", "substituted PropTS polymers" and "substituted ProDOS/DTS polymer") exhibit different colors in the reduced state that are blue shifted from conventional polypropylenedioxyselenophene, which is a deep blue.

The high optical transparency in the oxidized state is controlled by the conductivity of the polymer. Introduction of disorder into the structure is one method for decreasing interchain carrier mobility resulting in a decrease in the intensity of the optical transition occurring at the low energy of the near infrared region (NIR), one factor in obtaining a colorless oxidized state. By adding substitution at the 1, 3, or 1 and 3 positions of the 3,4-propylenedioxyselenophene and 3,4-propylenethioselenophene core will provide a disruption of conjugation of the polymer in order to increase the energy of the pi-pi* transition. The substitution will introduce steric interactions that would decrease interchain interactions of the polymer thereby increasing the optical transparency in the bleached state. Not wishing to be bound by theory, it is theorized the alpha substituents would project over the conjugated polymer backbone thereby causing steric interactions to distort selenophenes of the backbone out of planarity compared to unsubstituted 3,4-propylenedioxyselenopene/3,4-propylenethioselenophene polymers or even the 3,4-propylenedioxyselenopene polymers where the central carbon of ProDOS is substituted with alkyl groups. The distortion of planarity is expected to be proportional to the size of the substituent groups. Ditertbutyl substituents are expected to further blue shift the λmax with respect to the dimethyl substituents. As the substituent increases in size (e.g. increasing size of alkyl groups) it is anticipated that the polymer should transition to a highly transparent state in the semiconductive form. Longer alkyl substituents would further provide solubilization in organic solvents for improved solution processability.

Polymerized substituted ProDOS/DTS are excellent electrochromic materials in terms of their contrast ratios and Coloration Efficiency, while retaining stability and switching time characteristics comparable to those of PEDOT derivatives. The polymerized substituted ProDOS/DTS exhibit higher charge carrier mobilities compared to the analogous all-thiophene systems. The increased atomic radius of selenium (103 pm (picometer)) over sulfur (88 pm) enhances molecular overlaps between polymer chains, and facilitates the charge hopping process. The use of selenium results in a red-shift of the maximum absorbance wavelength over the all-thiophene systems (e.g. PEDOT). With proper substitution at the 1 and 3 positions of the substituted ProDOS/DTS, it is possible to make full color spectrum from a single molecular approach.

The polymerized substituted ProDOS/DTS will exhibit advantages over known conjugated polymers used for light display applications as light displays prepared thereform can easily be tuned in terms of color and color intensity. The substituted selenophene will have a lower oxidation potential and higher electron donating character than the sulfur analogue which helps the device to work at a lower potential window. Lower oxidation potential engenders high quality polymer films during electropolymerization by negating the harmful effects of high polymerization potentials which causes the degradation of the polymer films. Selenium is easier to polarize than sulfur, and is more suited to interchain charge transfer which should be facilitated by intermolecular Se . . . Se contacts.

The substituted ProDOS/DTS polymer exhibits low band gaps, can be p- and n-dopable as the selenium atom is more easily polarized than sulfur, the polymer is prepared from an electron rich monomer, and the substituted ProDOS/DTS polymer can be made processable from common organic solvents by proper choice of substituents.

The starting substituted ProDOS/DTS monomers used to prepare the substituted ProDOS/DTS polymers include those according to the general structure (I):

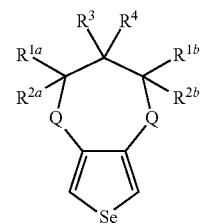

(I)

wherein each instance of Q is O or S; each of $R^{1a}$, $R^{1b}$, $R^{2a}$, $R^{2b}$, $R^3$, and $R^4$ independently is hydrogen; optionally substituted $C_1$-$C_{20}$ alkyl, $C_1$-$C_{20}$ haloalkyl, aryl, $C_1$-$C_{20}$ alkoxy, $C_1$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, —$C_1$-$C_{10}$ alkyl-aryl; or hydroxyl; with the proviso that at least one of $R^{1a}$, $R^{1b}$, $R^{2a}$, $R^{2b}$, $R^3$, and $R^4$ is not hydrogen, and when $R^{1a}$, $R^{1b}$, $R^{2a}$, and $R^{2b}$ are all hydrogen, then at least one of $R^3$ and $R^4$ is other than hydrogen, methyl, or ethyl. The $C_1$-$C_{20}$ alkyl, $C_1$-$C_{20}$ haloalkyl, aryl, $C_1$-$C_{20}$ alkoxy, $C_1$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, or —$C_1$-$C_{10}$ alkyl-aryl groups each may be optionally substituted with one or more of $C_1$-$C_{20}$ alkyl; aryl; halogen; hydroxyl; —N—$(R^7)_2$ wherein each $R^7$ is independently hydrogen or $C_1$-$C_6$ alkyl; cyano; nitro; —COOH; —S(═O) $C_0$-$C_{10}$ alkyl; or —S(═O)$_2$$C_0$-$C_{10}$ alkyl.

In one embodiment, each of $R^{1a}$, $R^{1b}$, $R^{2a}$ and $R^{2b}$ independently is $R^{1b}$ hydrogen; optionally substituted $C_1$-$C_{10}$ alkyl, $C_1$-$C_{10}$haloalkyl, aryl, $C_1$-$C_{10}$ alkoxy, $C_1$-$C_{10}$ haloalkoxy, aryloxy, —$C_1$-$C_5$ alkyl-O—$C_1$-$C_5$ alkyl, —$C_1$-$C_5$ alkyl-O-aryl, —$C_1$-$C_5$ alkyl-aryl; or hydroxyl; and $R^3$ and $R^4$ are both hydrogen; with the proviso that at least one of $R^{1a}$, $R^{1b}$, $R^{2a}$ and $R^{2b}$ is not hydrogen. The $C_1$-$C_{10}$ alkyl, $C_1$-$C_{10}$ haloalkyl, aryl, $C_1$-$C_{10}$ alkoxy, $C_1$-$C_{10}$ haloalkoxy, aryloxy, —$C_1$-$C_5$ alkyl-O—$C_1$-$C_5$ alkyl, —$C_1$-$C_5$ alkyl-O-aryl, or —$C_1$-$C_5$ alkyl-aryl groups each may be optionally substituted with one or more of $C_1$-$C_{20}$ alkyl; aryl; halogen; hydroxyl; —N—$(R^7)_2$ wherein each $R^7$ is independently hydrogen or $C_1$-$C_6$ alkyl; cyano; nitro; —COOH; —S(═O)$C_0$-$C_{10}$ alkyl; or —S(═O)$_2$$C_0$-$C_{10}$ alkyl.

In another embodiment, each of $R^{1a}$, $R^{1b}$, $R^{2a}$ and $R^{2b}$ independently is hydrogen; optionally substituted $C_1$-$C_5$ alkyl, $C_1$-$C_5$ haloalkyl, aryl, $C_1$-$C_5$ alkoxy, $C_1$-$C_5$ haloalkoxy, aryloxy, —$C_1$-$C_3$ alkyl-O—$C_1$-$C_3$ alkyl, —$C_1$-$C_3$ alkyl-O-aryl, —$C_1$-$C_3$ alkyl-aryl; or hydroxyl; and $R^3$ and $R^4$ are both hydrogen; with the proviso that at least one of $R^{1a}$, $R^{1b}$, $R^{2a}$ and $R^{2b}$ is not hydrogen. The $C_1$-$C_5$ alkyl, $C_1$-$C_5$ haloalkyl, aryl, $C_1$-$C_5$ alkoxy, $C_1$-$C_5$ haloalkoxy, aryloxy, —$C_1$-$C_3$ alkyl-O—$C_1$-$C_3$ alkyl, —$C_1$-$C_3$ alkyl-O-aryl, or —$C_1$-$C_3$ alkyl-aryl groups each may be optionally substituted with one or more of $C_1$-$C_{20}$ alkyl; aryl; halogen; hydroxyl; —N—$(R^7)_2$ wherein each $R^7$ is independently hydrogen or $C_1$-$C_6$ alkyl; cyano; nitro; —COOH; —S(═O)$C_0$-$C_{10}$ alkyl; or —S(═O)$_2$ $C_0$-$C_{10}$ alkyl.

In one embodiment, both Q groups are O. In another embodiment, both Q groups are S.

In one embodiment, at least two of $R^{1a}$, $R^{1b}$, $R^{2a}$, and $R^{2b}$ are not hydrogen while the remaining two groups are hydrogen. In an additional embodiment, both $R^{1a}$ and $R^{1b}$ or both $R^{2a}$ and $R^{2b}$ are hydrogen while the remaining two groups are other than hydrogen.

In one embodiment, each of $R^{1a}$, $R^{1b}$, $R^{2a}$, and $R^{2b}$ independently is hydrogen; or optionally substituted $C_1$-$C_{20}$ alkyl, $C_1$-$C_{20}$ haloalkyl, aryl, —$C_1$-$C_{10}$ alkyl-aryl; and $R^3$ and $R^4$ are both hydrogen; with the proviso that at least one of $R^{1a}$, $R^{1b}$, $R^{2a}$, and $R^{2b}$ is not hydrogen. The $C_1$-$C_{20}$ alkyl, $C_1$-$C_{20}$ haloalkyl, aryl, —$C_1$-$C_{10}$ alkyl-aryl groups each may be optionally substituted with one or more of $C_1$-$C_{20}$ alkyl; aryl; halogen; hydroxyl; —N—$(R^7)_2$ wherein each $R^7$ is independently hydrogen or $C_1$-$C_6$ alkyl; cyano; nitro; —COOH; —S(=O)$C_0$-$C_{10}$ alkyl; or —S(=O)$_2C_0$-$C_{10}$ alkyl.

In another embodiment, each of $R^{1a}$, $R^{1b}$, $R^{2a}$, and $R^{2b}$ independently is hydrogen; or optionally substituted $C_1$-$C_{20}$ alkyl, $C_1$-$C_{20}$ haloalkyl, aryl, —$C_1$-$C_{10}$ alkyl-aryl; and $R^3$ and $R^4$ are both hydrogen; with the proviso that at least two of $R^{1a}$, $R^{1b}$, $R^{2a}$, and $R^{2b}$ are not hydrogen. The $C_1$-$C_{20}$ alkyl, $C_1$-$C_{20}$ haloalkyl, aryl, —$C_1$-$C_{10}$ alkyl-aryl groups each may be optionally substituted with one or more of $C_1$-$C_{20}$ alkyl; aryl; halogen; hydroxyl; —N—$(R^7)_2$ wherein each $R^7$ is independently hydrogen or $C_1$-$C_6$ alkyl; cyano; nitro; —COOH; —S(=O)$C_0$-$C_{10}$ alkyl; or —S(=O)$_2C_0$-$C_{10}$ alkyl.

In yet another embodiment, $R^{1a}$, $R^{1b}$, $R^{2a}$, and $R^{2b}$ are all hydrogen; $R^3$, and $R^4$ are each independently optionally substituted $C_3$-$C_{20}$ alkyl, $C_3$-$C_{20}$ haloalkyl, aryl, $C_3$-$C_{20}$ alkoxy, $C_3$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, —$C_3$-$C_{10}$ alkyl-aryl; specifically substituted $C_4$-$C_{10}$ alkyl, $C_4$-$C_{10}$ haloalkyl, aryl, $C_4$-$C_{10}$ alkoxy, $C_4$-$C_{10}$ haloalkoxy, aryloxy, —$C_1$-$C_5$ alkyl-O—$C_1$-$C_5$ alkyl, —$C_1$-$C_5$ alkyl-O-aryl, —$C_4$-$C_8$ alkyl-aryl. In one embodiment, $R^{1a}$, $R^{1b}$, $R^{2a}$, and $R^{2b}$ are all hydrogen; $R^3$ and $R^4$ are both —$(CH_2)_3CH_3$; —$(CH_2)_7CH_3$; or —$CH_2OC(O)(CH_2)_5CH_3$.

The starting substituted ProDOS/DTS monomers to prepare the substituted ProDOS polymers include those according to the general structure (II):

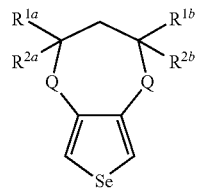
(II)

wherein Q, $R^{1a}$, $R^{1b}$, $R^{2a}$, and $R^{2b}$ are as described above.

In one embodiment, the substituted ProDOS/DTS monomer meets the general structure (II) wherein each of $R^{1a}$ and $R^{1b}$ independently is $C_1$-$C_{10}$ alkyl or benzyl and each of $R^{2a}$ and $R^{2b}$ independently is hydrogen, $C_1$-$C_{10}$ alkyl, or benzyl. In another embodiment, the substituted ProDOS/DTS monomer meets the general structure (II) wherein each of $R^{1a}$ and $R^{1b}$ independently is $C_1$-$C_5$ alkyl or benzyl and each of $R^{2a}$ and $R^{2b}$ independently is hydrogen, $C_1$-$C_5$ alkyl, or benzyl. In still yet another embodiment, the substituted ProDOS monomer meets the general structure (II) wherein each of $R^{1a}$ and $R^{1b}$ independently is $C_1$-$C_3$ alkyl or benzyl and each of $R^{2a}$ and $R^{2b}$ independently is hydrogen, $C_1$-$C_3$ alkyl, or benzyl. In yet another embodiment, the substituted ProDOS monomer meets the general structure (II) wherein each of $R^{1a}$ and $R^{1b}$ independently is methyl, isopropyl, tert-butyl, n-hexyl, or benzyl and each of $R^{2a}$ and $R^{2b}$ independently is hydrogen.

In other embodiments, the substituted ProDOS/DTS monomers include those according to the general structures (Ia) and (IIa)

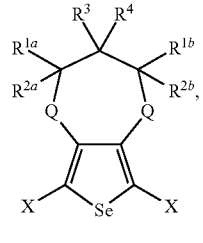
(Ia)

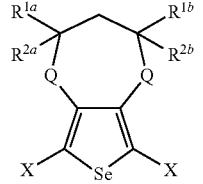
(IIa)

wherein Q, $R^{1a}$, $R^{1b}$, $R^{2a}$, and $R^{2b}$ are as described above and X is Cl, Br, or I.

The substituted ProDOS/DTS monomers can be prepared from a convenient synthetic path. In one embodiment, the substituted ProDOS monomers can be prepared via a transetherification reaction of 3,4-dialkoxyselenophene with an appropriately substituted diol according to the general Scheme A below.

Scheme A

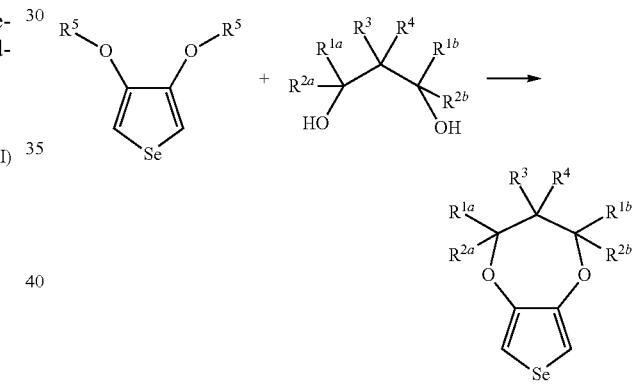

The starting 3,4-dialkoxyselenophene can have a lower alkyl substituent for $R^5$, specifically a $C_1$-$C_4$ alkyl, and more specifically a $C_1$-$C_2$ alkyl.

The substituted diol according to general Scheme A contains groups $R^{1a}$, $R^{1b}$, $R^{2a}$, $R^{2b}$, $R^3$, and $R^4$ as defined above, or their appropriately protected functional group equivalents. Commercially available diols include 2,4-pentanediol, 2-methyl-2,4-pentanediol, 2,4-dimethyl-2,4-pentanediol, 3-methyl-2,4-heptanediol, and 7-ethyl-2-methyl-4,6-nonanediol, all of which are available from Sigma-Aldrich The reaction of the 3,4-dialkoxyselenophene and diol is performed in the presence of a catalyst. Exemplary catalysts include sulfonic acids such as p-toluene sulfonic acid, dodecylbenzene sulfonic acid, and the like.

The solvent used in the reaction to prepare the substituted ProDOS monomer can be any high boiling, inert organic solvent including an aromatic such as toluene, xylene, and the like; and a halogenated aromatic including ortho-dichlorobenzene; mixtures thereof; and the like.

The temperature of the reaction to prepare the substituted ProDOS monomer can be at or about the boiling point of the solvent used. Specifically the reaction can be performed at temperatures of about 80 to about 300° C., more specifically about 90 to about 250° C., yet more specifically about 100 to about 200° C.

Substituted PropTS can be synthesized in an analogous fashion to ProDOS described above except that a dithiol is used. An exemplary dithiol is according to the structure

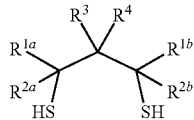

where $R^{1a}$, $R^{1b}$, $R^{2a}$, $R^{2b}$, $R^3$, and $R^4$ are as previously defined.

Exemplary ProDOS/DTS monomers include those provided in the following table.

Also disclosed herein are conductive conjugated polymers that are obtained via conversion of a substituted ProDOS/DTS monomer via chemical oxidation or electrochemical oxidation. These substituted ProDOS/DTS polymers have utilities in a wide variety of applications, for example, electronic packaging, organic light-emitting diodes (LEDs), electrochromic windows and displays, optically transparent electrodes, volatile organic gas sensors, as well as other applications discussed herein.

The substituted ProDOS/DTS monomers disclosed herein can be polymerized alone to form a conjugated homopolymer.

Also provided herein are copolymers comprising units derived from two or more different substituted ProDOS/DTS monomers. Also provided herein are copolymers comprising units derived from a substituted ProDOS/DTS and an additional monomer ("co-monomer") which provide a tailoring of

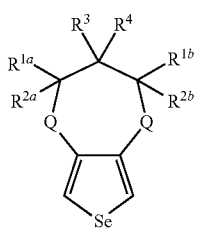

(I)

Structure (I)

| Q | $R^{1a}$ | $R^{2a}$ | $R^{1b}$ | $R^{2b}$ | $R^3$ | $R^4$ |
|---|---|---|---|---|---|---|
| O | —CH₃ | H | —CH₃ | H | H | H |
| O | —CH₃ | —CH₃ | —CH₃ | —CH₃ | H | H |
| O | —CH₂CH₃ | H | —CH₂CH₃ | H | H | H |
| O | —(CH₂)₂CH₃ | H | —(CH₂)₂CH₃ | H | H | H |
| O | —CH(CH₃)₂ | H | —CH(CH₃)₂ | H | H | H |
| O | —(CH₂)₃CH₃ | H | —(CH₂)₃CH₃ | H | H | H |
| O | —CH₂CH(CH₃)₂ | H | —CH₂CH(CH₃)₂ | H | H | H |
| O | —C(CH₃)₃ | H | —C(CH₃)₃ | H | H | H |
| O | —C₆H₁₃ | H | —C₆H₁₃ | H | H | H |
| O | —C₈H₁₇ | H | —C₈H₁₇ | H | H | H |
| O | CH(C₂H₅)(C₆H₁₃) | H | CH(C₂H₅)(C₆H₁₃) | H | H | H |
| O | —C₁₂H₂₅ | H | —C₁₂H₂₅ | H | H | H |
| O | —C₁₈H₃₇ | H | —C₁₈H₃₇ | H | H | H |
| O | —C₅H₉ | H | —C₅H₉ | H | H | H |
| O | —CH₂Ph | H | —CH₂Ph | H | H | H |
| O | —CH₂Ph | —CH₂Ph | —CH₂Ph | —CH₂Ph | H | H |
| S | —CH₃ | H | —CH₃ | H | H | H |
| S | —CH₃ | —CH₃ | —CH₃ | —CH₃ | H | H |
| S | —CH₂CH₃ | H | —CH₂CH₃ | H | H | H |
| S | —(CH₂)₂CH₃ | H | —(CH₂)₂CH₃ | H | H | H |
| S | —CH(CH₃)₂ | H | —CH(CH₃)₂ | H | H | H |
| S | —(CH₂)₃CH₃ | H | —(CH₂)₃CH₃ | H | H | H |
| S | —CH₂CH(CH₃)₂ | H | —CH₂CH(CH₃)₂ | H | H | H |
| S | —C(CH₃)₃ | H | —C(CH₃)₃ | H | H | H |
| S | —C₆H₁₃ | H | —C₆H₁₃ | H | H | H |
| S | —C₈H₁₇(CH₂)₇CH₃ | H | —C₈H₁₇(CH₂)₇CH₃ | H | H | H |
| S | —CH₂Ph | H | —CH₂Ph | H | H | H |
| S | —CH₂Ph | —CH₂Ph | —CH₂Ph | —CH₂Ph | H | H |
| S | CH(C₂H₅)(C₆H₁₃) | H | CH(C₂H₅)(C₆H₁₃) | H | H | H |
| S | —C₁₂H₂₅ | H | —C₁₂H₂₅ | H | H | H |
| S | —C₁₈H₃₇ | H | —C₁₈H₃₇ | H | H | H |
| S | —C₅H₉ | H | —C₅H₉ | H | H | H |
| O | H | H | H | H | —(CH₂)₃CH₃ | —(CH₂)₃CH₃ |
| O | H | H | H | H | —(CH₂)₇CH₃ | —(CH₂)₇CH₃ |
| O | H | H | H | H | —CH₂OC(O)(CH₂)₅CH₃ | —CH₂OC(O)(CH₂)₅CH₃ |
| O | H | H | H | H | —CH₂O(2-EthylHexyl) | —CH₂O(2-EthylHexyl) |
| O | H | H | H | H | CH₂Ph | CH₂Ph |
| S | H | H | H | H | —(CH₂)₃CH₃ | —(CH₂)₃CH₃ |
| S | H | H | H | H | —(CH₂)₇CH₃ | —(CH₂)₇CH₃ |
| S | H | H | H | H | —CH₂OC(O)(CH₂)₅CH₃ | —CH₂OC(O)(CH₂)₅CH₃ |
| S | H | H | H | H | —CH₂O(2-EthylHexyl) | —CH₂O(2-EthylHexyl) |
| S | H | H | H | H | CH₂Ph | CH₂Ph | the conductivity or optoelectronic properties of the resulting polymer. The co-monomer can include electroactive monomers or non-electroactive monomers. "Electroactive monomer" as used herein means a monomer or oligomer that is capable of copolymerization with substituted ProDOS/DTS, and that imparts or enhances the electrical/electronic properties of the resulting copolymer, including such properties as electrical conductivity, semiconductivity, electroluminescence, electrochromicity, photovoltaic properties, or the like. "Non-electroactive monomer" means a monomer that is capable of copolymerization and that either decreases or does not adversely affect the electrical/electronic properties of the resulting copolymer.

Examples of suitable electroactive monomers include those known in the art to exhibit electroactivity, including but not limited to thiophene, substituted thiophene, thieno[3,4-b]thiophene, substituted thieno[3,4-b]thiophene, dithieno[3,4-b:3',4'-d]thiophene, thieno[3,4-b]furan, substituted thieno[3,4-b]furan, bithiophene, substituted bithiophene, selenophene, substituted selenophene, pyrrole, substituted pyrrole, phenylene, substituted phenylene, naphthalene, substituted naphthalene, biphenyl and terphenyl and their substituted versions, phenylene vinylene, substituted phenylene vinylene, and the like.

Suitable co-monomers include unsubstituted and 2- or 6-substituted thieno[3,4-b]thiophene and thieno[3,4-b]furan having the general structures (III), (IV), and (V):

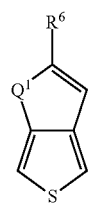

(III)

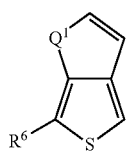

(IV)

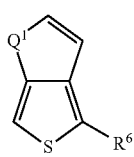

(V)

wherein $Q^1$ is S or O; and $R^6$ is hydrogen, $C_1$-$C_{12}$ alkyl, $C_1$-$C_{12}$ haloalkyl including perfluoroalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl. Specifically, $Q^1$ is S or O; and $R^6$ is hydrogen.

Derivatives having the general structures (VI), (VII), and (VIII):

(VI)

(VII)

(VIII)

wherein $G^1$ is S or Se; $G^2$ is S, Se, or O wherein at least one of $G^1$ or $G^2$ is Se; and $R^6$ is hydrogen, $C_1$-$C_{12}$ alkyl, $C_1$-$C_{12}$ haloalkyl including perfluoroalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl. Specifically, $G^1$ is S or Se; $G^2$ is S or Se; and $R^6$ is hydrogen.

3,4-Ethylenedioxythiophene, 3,4-ethylenedithiathiophene, 3,4-ethylenedioxypyrrole, 3,4-ethylenedithiapyrrole, 3,4-ethylenedioxyfuran, 3,4-ethylenedithiafuran, and derivatives having the general structure (IX):

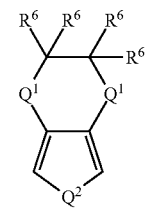

(IX)

wherein each occurrence of $Q^1$ is independently S or O; $Q^2$ is S, O, or N—$R^7$ wherein $R^7$ is hydrogen or $C_1$-$C_6$ alkyl; and each occurrence of $R^6$ is hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Seleno derivatives having the general structure (X):

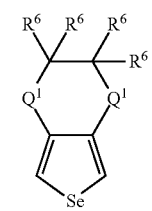

(X)

wherein each occurrence of $Q^1$ is independently S or O; and each occurrence of $R^6$ is hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Isathianaphthene, pyridothiophene, pyrizinothiophene, and derivatives having the general structure (XI):

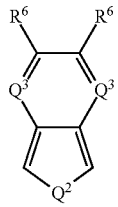

(XI)

wherein $Q^2$ is S, O, or N—$R^7$ wherein $R^7$ is hydrogen or $C_1$-$C_6$ alkyl; each occurrence of $Q^3$ is independently CH or N; and each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Oxazole, thiazole, and derivatives having the general structure (XII):

(XII)

wherein $Q^1$ is S or O.

Pyrrole, furan, thiophene, and derivatives having the general structure (XIII):

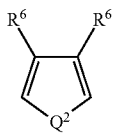

(XIII)

wherein $Q^2$ is S, O, or N—$R^7$ wherein $R^7$ is hydrogen or $C_1$-$C_6$ alkyl; and each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Selenophene and derivatives having the general structure (XIV):

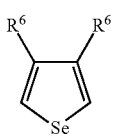

(XIV)

wherein each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Bithiophene, bifuran, bipyrrole, and derivatives having the following general structure (XV):

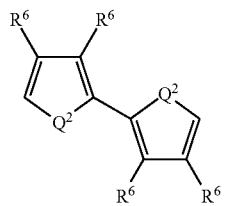

(XV)

wherein each occurrence of $Q^2$ is independently S, O, or N—$R^7$ wherein $R^7$ is hydrogen or $C_1$-$C_6$ alkyl; and each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Biselenophene and derivatives having the following general structure (XVI):

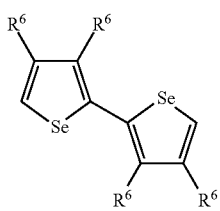

(XVI)

wherein each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Terthiophene, terfuran, terpyrrole, and derivatives having the following general structure (XVII):

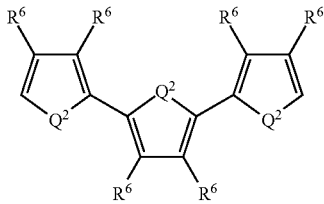

(XVII)

wherein each occurrence of $Q^2$ is independently S, O, or N—$R^7$ wherein $R^7$ is hydrogen or $C_1$-$C_6$ alkyl; and each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Terselenophene and derivatives having the following general structure (XVIII):

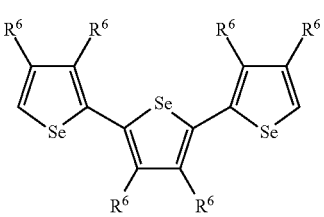

(XVIII)

wherein each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Thienothiophene, thienofuran, thienopyrrole, furanylpyrrole, furanylfuran, pyrolylpyrrole, and derivatives having the following general structure (XIX):

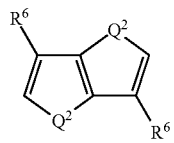

(XIX)

wherein each occurrence of $Q^2$ is independently S, O, or N—$R^7$ wherein $R^7$ is hydrogen or $C_1$-$C_6$ alkyl; and each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Dithienothiophene, difuranylthiophene, dipyrrolylthiophene, dithienofuran, dipyrrolylfuran, dipyrrolylpyrrole, and derivatives having the following general structure (XX):

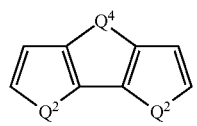

(XX)

wherein each occurrence of $Q^2$ is independently S, O, or N—$R^7$ wherein $R^7$ is hydrogen or $C_1$-$C_6$ alkyl; $Q^4$ is $C(R^6)_2$, S, O, or N—$R^7$; and each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Dithienylcyclopentenone, difuranylcyclopentenone, dipyrrolylcyclopentenone and derivatives having the following general structure (XXI):

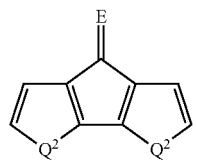

(XXI)

wherein each occurrence of $Q^2$ is independently S, O, or N—$R^7$ wherein $R^7$ is hydrogen or $C_1$-$C_6$ alkyl; and E is O or $C(R^8)_2$, wherein each occurrence of $R^8$ is an electron withdrawing group.

Other suitable heteroaryl monomers include those having the following general structure (XXII):

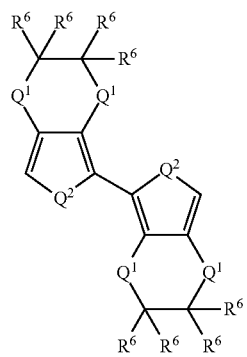

(XXII)

wherein each occurrence of $Q^1$ is independently S or O; each occurrence of $Q^2$ is independently S, O, or N—$R^7$ wherein $R^7$ is hydrogen or $C_1$-$C_6$ alkyl; each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl. In one embodiment, each occurrence of $Q^1$ is O; each occurrence of $Q^2$ is S; and each occurrence of $R^6$ is hydrogen.

Seleno derivatives having the following general structure (XXIII):

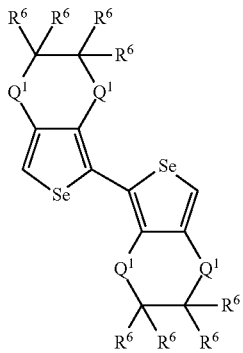

(XXIII)

wherein each occurrence of $Q^1$ is independently S or O; each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl. In one embodiment, each occurrence of $Q^1$ is O and each occurrence of $R^6$ is hydrogen.

Dithienovinylene, difuranylvinylene, and dipyrrolylvinylene according to the structure (XXIV):

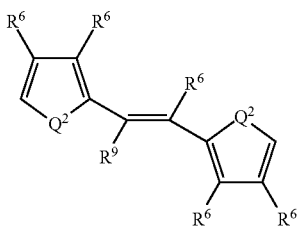

(XXIV)

wherein each occurrence of $Q^2$ is independently S, O, or N—$R^7$ wherein $R^7$ is hydrogen or $C_1$-$C_6$ alkyl; each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl; and each occurrence of $R^9$ is hydrogen, $C_1$-$C_6$ alkyl, or cyano.

1,2-Trans(3,4-ethylenedioxythienyl)vinylene, 1,2-trans(3,4-ethylenedioxyfuranyl)vinylene, 1,2-trans(3,4-ethylenedioxypyrrolyl)vinylene, and derivatives according to the structure (XXV):

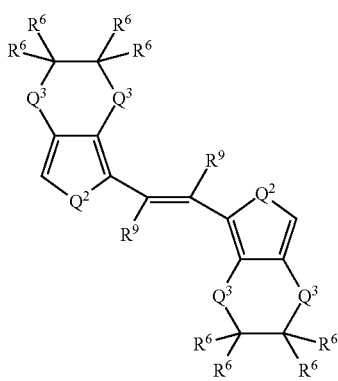

(XXV)

wherein each occurrence of $Q^3$ is independently $CH_2$, S, or O; each occurrence of $Q^2$ is independently S, O, or N—$R^7$ wherein $R^7$ is hydrogen or $C_1$-$C_6$ alkyl; each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl; and each occurrence of $R^9$ is hydrogen, $C_1$-$C_6$ alkyl, or cyano.

The class bis-thienylarylenes, bis-furanylarylenes, bis-pyrrolylarylenes and derivatives according to the structure (XXVI):

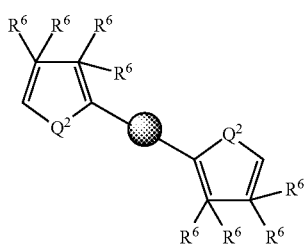

(XXVI)

wherein each occurrence of $Q^2$ is independently S, O, or N—$R^7$ wherein $R^7$ is hydrogen or $C_1$-$C_6$ alkyl; each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl; and

represents an aryl. Exemplary aryl groups include furan, pyrrole, N-substituted pyrrole, phenyl, biphenyl, thiophene, fluorene, 9-alkyl-9H-carbazole, and the like.

The class of bis(3,4-ethylenedioxythienyl)arylenes, related compounds, and derivatives according to the structure (XXVII):

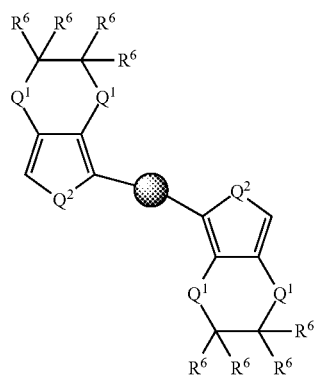

(XXVII)

wherein each occurrence of $Q^1$ is independently S or O; each occurrence of $Q^2$ is independently S, O, or N—$R^7$ wherein $R^7$ is hydrogen or $C_1$-$C_6$ alkyl; each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl; and

represents an aryl.

An exemplary bis(3,4-ethylenedioxythienyl)arylenes according to structure (XXVII) includes the compound wherein all $Q^1$ are O, both $Q^2$ are S, all $R^6$ are hydrogen, and

is phenyl linked at the 1 and 4 positions. Another exemplary compound is where all $Q^1$ are O, both $Q^2$ are S, all $R^6$ are hydrogen, and

is thiophene linked at the 2 and 5 positions.

The class of compounds according to structure (XXVIII):

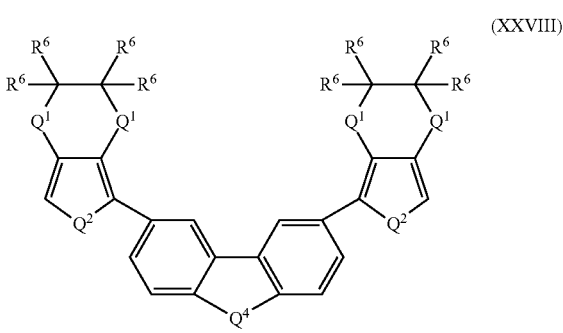

(XXVIII)

wherein each occurrence of $Q^1$ is independently S or O; each occurrence of $Q^2$ is independently S, O, or N—$R^7$ wherein $R^7$ is hydrogen or $C_1$-$C_6$ alkyl; $Q^4$ is $C(R^6)_2$, S, O, or N—$R^7$; and each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl. In one embodiment, each occurrence of $Q^1$ is O; each occurrence of $Q^2$ is S; each occurrence of $R^6$ is hydrogen; and $R^7$ is methyl.

The class of compounds according to structure (XXIX):

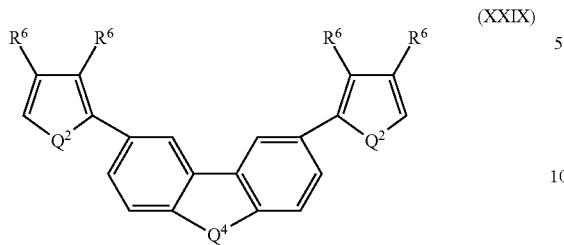

(XXIX)

wherein each occurrence of $Q^2$ is independently S, O, or N—$R^7$ wherein $R^7$ is hydrogen or $C_1$-$C_6$ alkyl; $Q^4$ is $C(R^6)_2$, S, O, or N—$R^7$; and each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

The class of compounds according to structure (XXX):

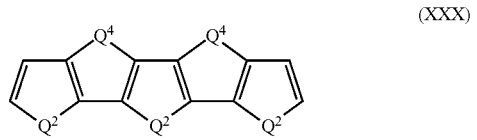

(XXX)

wherein each occurrence of $Q^2$ is independently S, O, or N—$R^7$ wherein $R^7$ is hydrogen or $C_1$-$C_6$ alkyl; each occurrence of $Q^4$ is $C(R^6)_2$, S, O, or N—$R^7$; and each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

The class of compounds according to structure (XXXI):

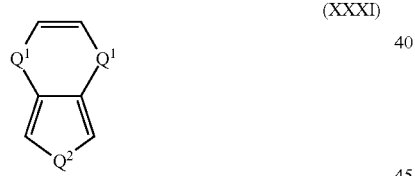

(XXXI)

wherein $Q^2$ is S, O, or N—$R^7$ wherein $R^7$ is hydrogen or $C_1$-$C_6$ alkyl; and each occurrence of $Q^1$ is independently S or O.

The class of compounds according to structure (XXXII):

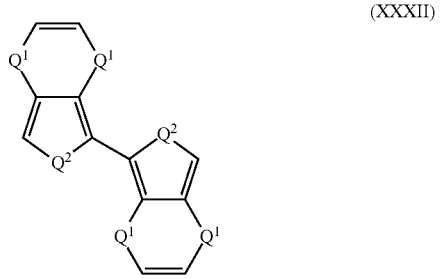

(XXXII)

wherein each occurrence of $Q^2$ is independently S, O, or N—$R^7$ wherein $R^7$ is hydrogen or $C_1$-$C_6$ alkyl; and each occurrence of $Q^1$ is independently S or O.

The class of compounds according to structure (XXXIII):

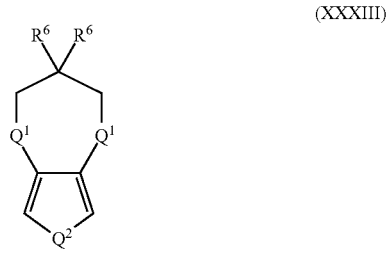

(XXXIII)

wherein $Q^2$ is S, O, or N—$R^7$ wherein $R^7$ is hydrogen or $C_1$-$C_6$ alkyl; each occurrence of $Q^1$ is independently S or O; and each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, —$C_1$-$C_6$ alkyl-aryl, —$C_1$-$C_6$ alkyl-O-aryl, or —$C_1$-$C_6$ alkyl-O-aryl. In one embodiment, one $R^6$ is methyl and the other $R^6$ is benzyl, —$C_1$-$C_6$ alkyl-O-phenyl, —$C_1$-$C_6$ alkyl-O-biphenyl, or —$C_1$-$C_6$ alkyl-biphenyl.

The class of compounds according to structure (XXXIV):

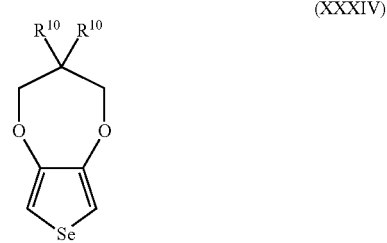

(XXXIV)

wherein each occurrence of $R^{10}$ is independently hydrogen, methyl, ethyl, or benzyl.

The class of compounds according to structure (XXXV):

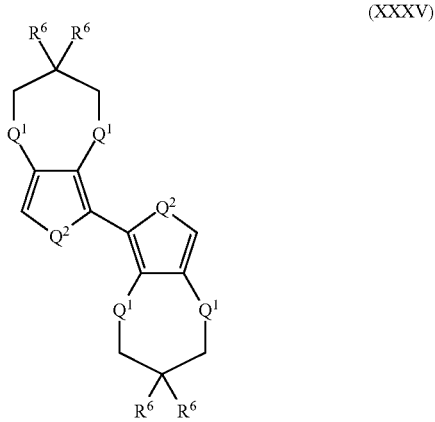

(XXXV)

wherein each occurrence of $Q^2$ is independently S, O, or N—$R^7$ wherein $R^7$ is hydrogen or $C_1$-$C_6$ alkyl; each occurrence of $Q^1$ is independently S or O; and each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or $C_1$-$C_6$ alkyl-O-aryl. In one embodiment, one $R^6$ is methyl and the other $R^6$ is —$C_1$-$C_6$ alkyl-O-phenyl or —$C_1$-$C_6$ alkyl-O-biphenyl per geminal carbon center.

The class of compounds according to structure (XXXVI):

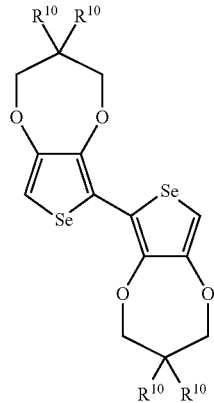

(XXXVI)

wherein each occurrence of $R^{10}$ is independently hydrogen, methyl, ethyl, or benzyl.

The class of compounds according to structure (XXXVII):

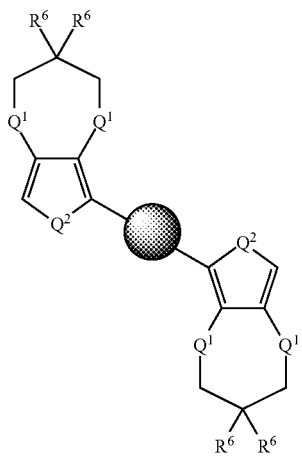

(XXXVII)

 represents an aryl. In one embodiment, one $R^6$ is methyl and the other $R^6$ is —$C_1$-$C_6$ alkyl-O-phenyl or —$C_1$-$C_6$ alkyl-O-biphenyl per geminal carbon center.

wherein each occurrence of $Q^2$ is independently S, O, or N—$R^7$ wherein $R^7$ is hydrogen or $C_1$-$C_6$ alkyl; each occurrence of $Q^1$ is independently S or O; each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or $C_1$-$C_6$ alkyl-O-aryl; and The class of compounds according to structure (XXXVIII):

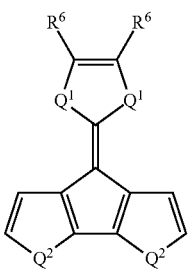

(XXXVIII)

wherein each occurrence of $Q^2$ is independently S, O, or N—$R^7$ wherein $R^7$ is hydrogen or $C_1$-$C_6$ alkyl; each occurrence of $Q^1$ is independently S or O; and each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

The class of compounds according to structure (XXXIX):

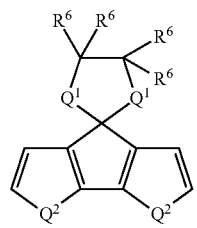

(XXXIX)

wherein each occurrence of $Q^2$ is independently S, O, or N—$R^7$ wherein $R^7$ is hydrogen or $C_1$-$C_6$ alkyl; each occurrence of $Q^1$ is independently S or O; and each occurrence of $R^6$ is independently hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

In one embodiment, the copolymer comprises 1 to about 99 percent substituted ProDOS/DTS monomer units, specifically about 20 to about 90 percent, more specifically about 30 to about 80 percent, and yet more specifically about 40 to about 70 percent substituted ProDOS/DTS monomer units present in the copolymer based on the total units of the copolymer.

As used herein, "alkyl" includes straight chain, branched, and cyclic saturated aliphatic hydrocarbon groups, having the specified number of carbon atoms, generally from 1 to about 20 carbon atoms, specifically about 3 to about 15, and more specifically about 5 to about 10 for the straight chain; and generally from 3 to about 20 carbon atoms, specifically about 4 to about 16, and more specifically about 6 to about 12 for the branched and cyclic. Examples of alkyl include, but are not limited to, methyl, ethyl, n-propyl, isopropyl, n-butyl, 3-methylbutyl, t-butyl, n-pentyl, sec-pentyl, cyclopentyl, cyclohexyl, and octyl. Specific alkyl groups include lower alkyl groups, those alkyl groups having from 1 to about 8 carbon atoms, from 1 to about 6 carbon atoms, or from 1 to about 4 carbons atoms.

As used herein "haloalkyl" indicates straight chain, branched, and cyclic alkyl groups having the specified number of carbon atoms, substituted with 1 or more halogen atoms, generally up to the maximum allowable number of halogen atoms ("perhalogenated", e.g. perfluorinated). Examples of haloalkyl include, but are not limited to, trifluoromethyl, difluoromethyl, 2-fluoroethyl, and penta-fluoroethyl.

As used herein, "alkoxy" includes an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Haloalkoxy" indicates a haloalkyl group as defined above attached through an oxygen bridge.

As used herein, the term "aryl" indicates aromatic groups containing only carbon in the aromatic ring or rings. Such aromatic groups may be further substituted with carbon or non-carbon atoms or groups. Typical aryl groups contain 1 or 2 separate, fused, or pendant rings and from 6 to about 12 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, anthracene, pentacene, fluorene, and bi-phenyl.

"Halo" or "halogen" as used herein refers to fluoro, chloro, bromo, or iodo.

Compounds are described using standard nomenclature. For example, any position not substituted by any indicated group is understood to have its valency filled by a bond as indicated, or a hydrogen atom. A dash ("—") that is not between two letters or symbols is used to indicate a point of attachment for a substituent. For example, —CHO is attached through carbon of the carbonyl group.

Also contemplated herein are blends comprising two or more substituted ProDOS/DTS polymers. Additionally, blends comprising at least one of the foregoing substituted ProDOS/DTS polymers and an additional polymer are also contemplated. The additional polymer may be a conductive polymer, a nonconductive polymer, a thermoplastic or combinations comprising at least one of the foregoing.

In one method, a substituted ProDOS/DTS monomer and an optional co-monomer is chemically oxidized in a liquid to form the substituted ProDOS/DTS polymer. Suitable oxidants include the iron (III) salts of organic acids, inorganic acids containing organic residues, and inorganic acids, such as $FeCl_3$, $Fe(ClO_4)_3$. Oxidants such as $H_2O_2$, $K_2Cr_2O_7$, alkali or ammonium persulfates, alkali perborates, potassium permanganate, $NOBF_4$, or copper salts such as copper tetrafluoroborate may also be used. In addition, bromine, iodine, and oxygen may advantageously be used as oxidants. Persulfates and the iron (III) salts of organic acids and inorganic acids containing organic residues can be used because they are not corrosive. Examples of suitable iron (III) salts of organic acids are the Fe(III) salts of $C_1$-$C_{30}$ alkyl sulfonic acids, such as methane or dodecane sulfonic acid; aliphatic $C_1$-$C_{20}$ carboxylic acids, such as 2-ethylhexylcarboxylic acid; aliphatic $C_1$-$C_{20}$ perfluorocarboxylic acids, such as trifluoroacetic acid and perfluorooctanoic acid; aliphatic dicarboxylic acids, such as oxalic acid; and aromatic, optionally $C_1$-$C_{20}$ alkyl-substituted sulfonic acids, such as benzenesulfonic acid, p-toluenesulfonic acid and dodecyl benzenesulfonic acid. Mixtures of the aforementioned Fe(III) salts of organic acids may also be used. Examples of iron (III) salts of inorganic acids containing organic residues are the iron (III) salts of sulfuric acid semesters of $C_1$-$C_{20}$ alkanols, for example the Fe(III) salt of lauryl sulfate.

Suitable liquids for conducting the oxidative chemical reaction are those that do not adversely affect the reaction, and specifically are inert. Suitable liquids can further be selected on the basis of economics, environmental factors, and the like, and may be organic, aqueous, or a mixture thereof. Suitable organic liquids may be aliphatic alcohols such as methanol and ethanol; aliphatic ketones such as acetone and methyl ethyl ketone; aliphatic carboxylic esters such as ethyl acetate; aromatic hydrocarbons such as toluene and xylene; aliphatic hydrocarbons such as hexane; aliphatic nitriles such as acetonitrile; chlorinated hydrocarbons such as dichloromethane; aliphatic sulfoxides such as dimethyl sulfoxide; and the like, as well as mixtures comprising at least one of the foregoing organic liquids. Specifically aqueous liquids are used, that is, a liquid comprising water or water-miscible organic liquids such as lower alcohols, acetonitrile, tetrahydrofuran, dimethylacetamide, dimethylformamide, and the like.

Heat may not be necessary for the formation of the substituted ProDOS polymer in the chemical oxidation process. However, it can be used to speed up the conversion to the conjugated polymers. Heat can be administered to the reaction medium either during its exposure to chemical oxidants or after the exposure. Typical reaction conditions include temperatures of about 0 to about 100° C. The oxidation is continued for a period of time until the desired conjugated polymer is prepared. The polymerization time may be a few minutes up to about 48 hours, and depends on a number of factors including the size of the reactor utilized, the reaction temperature, the oxidant utilized, and the like.

In one embodiment, a substituted ProDOS monomer and an optional co-monomer is converted to a conjugated polymer by a chemical oxidant such as $FeCl_3$ or those previously discussed. When a chemical oxidant is used, the addition of a salt to the reaction solution can be used to get adequate oxidation. Suitable salts for this purpose include organic soluble salts, inorganic salts, ionic liquids, and polyelectrolytes such as polystyrene sulfonate, polyacrylic acid sodium salt, poly(meth)acrylic acid sodium salt, etc. Exemplary salts include tetra-alkyl ammonium, ammonium, lithium, or sodium cations with tetrafluoroborate, hexafluorophosphate, perchlorate, halides, toluenesulfonate and other aliphatic sulfonate salts, trifluoromethylsulfonate, bistrifluoromethanesulfonimide, sulfates, carbonates or persulfates.

An alternative method for preparing the substituted ProDOS/DTS polymer is by electrochemical oxidation to convert a substituted ProDOS/DTS monomer and an optional co-monomer to a conjugated polymer. Conventional electrolytic cells can be used for the reaction. In one embodiment, a three-electrode configuration (working electrode, counter electrode, and reference electrode) in operable communication with an electrolyte is used, comprising a working electrode, specifically a button working electrode selected from the group consisting of platinum, gold, vitreous carbon, and indium doped tin oxide working electrodes or non-button electrodes such as the ITO, and platinum flag, a platinum flag counter electrode, and an Ag/Ag+ non-aqueous reference electrode.

Suitable electrolytes include tetraalkylammonium salts, e.g., tetraethylammonium, tetrapropyl ammonium, tetrabutylammonium salts, as well as salts of cations such as lithium trifluoromethansulfonate. Suitable counter ions include but are not limited inorganic ions such as bistrifluoromethylsulfonimide, tosylate, perchlorate, tetrafluoroborate, hexafluorophosphate, and halides such as chloride, bromide, iodide, and organic anions such as tosylate, triflate, trifluoromethylsulfonimide, or polyanions, e.g., polystyrenesulfonate, the anionic form of acrylic acid. Solvents may be used to prepare an electrolyte solution, for example water, ethanol, methanol, acetonitrile, propylene carbonate, tetraglyme, methylene chloride, chloroform, and tetrahydrofuran. Specified solvents are water, acetonitrile, and propylene carbonate.

Other suitable electrolytes include ionic liquids such as butylmethylimidazolium hexafluorophosphate (BMIM $PF_6$) and butylmethylimidizolium tetrafluoroborate (BMIM $BF_4$).

Specified electrolytes include tetrabutylammonium perchlorate/acetonitrile, tetrabutylammonium tetrafluoroborate, tetrabutylammonium hexafluorophosphate/acetonitrile, lithium trifluoromethansulfonate/acetonitrile, and lithium triflate/acetonitrile. Exemplary concentrations of the electrolytes are about 0.05 to about 0.15, specifically about 0.1 M.

A specified working electrode is a vitreous carbon electrode and the electrolyte is tetrabutylammonium hexafluorophosphate/acetonitrile. Another specified working electrode is a platinum button electrode and the electrolyte is tetrabutylammonium hexafluorophosphate/acetonitrile.

The substituted ProDOS/DTS polymers disclosed herein provide for a transition from pure blue to colorless.

The electrical conductivity of the films prepared from the polymers can be readily modified, if necessary, to meet the requirements of a desired application by doping with conventional acidic dopants (p-dopants) or basic dopants (n-dopants) known in the art. Suitable p-dopants include mineral acids such as HCl, $HNO_3$, $H_2SO_4$, $H_3PO_4$, HBr, and HI; organic sulfonic acids such as dodecyl benzene sulfonic acid, lauryl sulfonic acid, camphor sulfonic acid, organic acid dyes, methane sulfonic acid, and toluene sulfonic acid; polymeric sulfonic acids such as poly(styrene sulfonic acid) and copolymers of styrene sulfonic acids; carboxylic acids such as adipic acid, azelaic acid, and oxalic acid; and polycarboxylic acids such as poly(acrylic acid), poly(maleic acid), poly (methacrylic acid), and copolymers formed from acrylic acid, maleic acid, or methacrylic acid. Conventional mixed dopants comprising one or more of the foregoing, such as a mixture of a mineral acid and an organic acid, can also be used to impart the desired electroactive character to the films. Suitable basic dopants include, but are not limited to Na, K, Li, and Ca. Other suitable dopants include $I_2$, $PF_6$, $SbF_6$, and $FeCl_3$. In some instances the oxidant and the dopant may be the same.

Admixtures of the polymer with other electroactive materials such as laser dyes, other electroactive polymers, hole transport or electron transport materials, including electroactive organometallic compounds, are also contemplated herein. Such materials can be added to the polymer before or after formation of the solution or dispersion. Additives such as ethylene glycol, diethylene glycol, mannitol, propylene 1,3-glycol, butane 1,4-glycol, N-methylpyrrolidone, sorbitol, glycerol, propylene carbonate, and other appropriate high boiling organics may be added to dispersions of the polymeric compositions to improve conductivity.

Additional additives may also be used, and include conductive fillers such as particulate copper, silver, nickel, aluminum, carbon black (carbon nanotubes, buckminister fullerene), and the like; non-conductive fillers such as talc, mica, wollastonite, silica, clay, dyes, pigments (zeolites), and the like, to promote specific properties such as increased modulus, surface hardness, surface color and the like; antioxidants; UV stabilizers; viscosity modifiers; and surfactants such as acetylenic diols, surfactants typically being added to control stability, surface tension, and surface wettability.

The substituted ProDOS/DTS polymers are especially useful as charge transport or semiconductor materials The substituted ProDOS/DTS polymers disclosed herein can be processed by conventional methods to provide uniform, thin films that possess utility in numerous applications. Films and materials comprising the above-described conjugated polymers can be utilized in a variety of applications, including antistatic coatings, electrically conductive coatings, electrochromics, photovoltaic devices, light emitting diodes for display applications, hole injection layers for light emitting diodes, near infrared light emitting diodes, transparent conductive coating for indium doped tin oxide replacement, flat panel displays, flexible displays, photoimageable circuits, printable circuits, thin film transistor devices, batteries, electrical switches, capacitor coatings, corrosion resistant coatings, electromagnetic shielding, sensors, biosensors, dimmable mirrors, type III supercapacitors, LED lighting, and the like, and specifically electrochromic windows, electrochromic films for reflective devices, and electrochromic displays. The electrical conductivity of the polymers can be readily modified, if necessary, to meet the requirements of any of the previously mentioned applications by doping the polymers with conventional dopants such as anions (for p-doped polymers) and cation dopants (for n-doped polymers) known in the art.

The substituted ProDOS/DTS polymers find particular application in the electrochromic devices with enhanced photopic contrast.

The following illustrative examples are provided to further describe how to make and use the polymers and are not intended to limit the scope of the claimed invention.

EXAMPLES

Example 1

Preparation of meso-2,2,6,6-Tetramethyl-3,5-heptanediol (TMHDiol) (3)

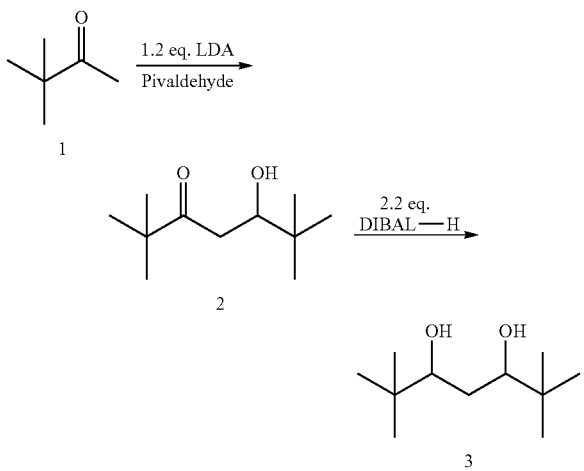

5-Hydroxy-2,2,6,6,-tetramethyheptan-3-one (HTMH-One) (2): To a solution of pinacolone (10 g, 100 mmol, 1), in anhydrous THF (500 mL), at −78° C. a 2.0 M solution of lithium diisopropylamide (LDA) in hexane (60 mL, 120 mmol) over a period of 30 min. The reaction was stirred at −78° C. for another 30 min. To the resulting white suspension pivalaldehyde (10.9 mL, 100 mmol) was added drop-wise via syringe and the reaction continued for another 12 hrs at room temperature. The reaction was quenched by adding 10 mL of water. Approximately 80% THF was removed and the mixture was then poured into saturated aqueous solution of NH$_4$Cl. The aqueous layer was extracted twice with diethyl ether (200 mL) and the organic layer was washed with plenty of water. The organic layer was then dried over MgSO$_4$ and concentrated to give a crude yellow solid of β-hydroxy ketone (17.2 g, 95%, (2)). The crude product was recrystallized from hexane to give pure white solid with a yield of 81%.

Meso-2,2,6,6-Tetramethyl-3,5-heptanediol (TMHDio1) (3): To a solution of β-hydroxy ketone (10 g, 53 mmol, (2)) in THF (250 mL) was added 1 M Diisobutylaluminium hydride (DIBAL-H) in hexane, (118 mL, 118 mmol) at −78° C., and the solution was stirred for 2 hrs at this temperature. The reaction mixture was allowed to warm to room temperature and continued for another 8 hrs at room temperature. After 8 hrs the reaction mixture was quenched with 2 N aqueous HCl solution. The mixture was then extracted twice with ether (200 mL), and the combined organic layer was washed with saturated aqueous NaHCO$_3$ solution and with brine. Drying with anhydrous MgSO$_4$ and concentration gave the TMHDiol (9 g, 90% yield, (3)) as a white solid.

Example 2

Preparation of 2,2-dihexyl Propane-1,3-diol (6)

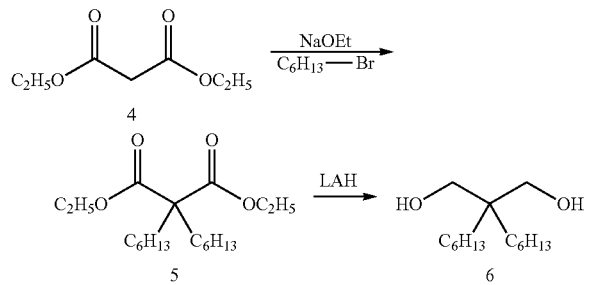

Synthesis of 2,2-Dihexylmalonic Acid Diethyl Ester (5): In a 500 mL flame dried three-neck round bottom flask equipped with an argon inlet and condenser were combined 200 mL of dry THF, hexyl bromide (0.00 g, 1.5 mole), and 3.5 mol of NaH. The flask was cooled to 0° C., and 1.15 mol of freshly distilled diethylmalonate (4) was added dropwise via syringe. After the addition of malonate, the mixture was refluxed for 12 h. The flask was then cooled at 0° C. and the remaining sodium hydride was quenched by adding water dropwise. The mixture was then poured into brine solution (2 L) and extracted two times with ether. The ether layer was finally washed with brine and then with water. The organic phase was dried over MgSO$_4$, and evaporated to give a light yellow liquid. The crude product was further purified by vacuum distillation to provide 2,2-dihexylmalonic acid diethyl ester (0.85 g, 70%, (5)) as a colorless oil.

Synthesis of 2,2-Dihexyl Propane-1,3-diol (6): A suspension of lithium aluminum hydride (LAH) (2 g, 52.6 mmol) in dry THF (20 mL) was stirred at room temperature, and a THF solution of substituted malonic acid diethyl ester (26.3 mmol, (5)) was added dropwise. The reaction was allowed to reflux for 3 h and was quenched by the addition of cold water. The compound was extracted in ethyl acetate. The organic layer was washed with water, dried over Na2SO4, and evaporated to produce the product (6) as either a sticky liquid or a low-melting solid.

Example 3

Preparation of (3R,5S)-2,6-dimethylheptane-3,5-diol(DMH-Diol)

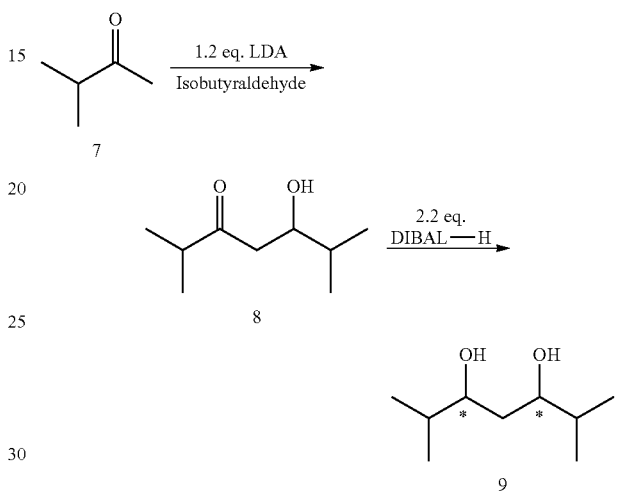

5-hydroxy-2,6-dimethylheptan-3-one (HDMH-One): To a solution of 3-methylbutan-2-one (10 g, 116 mmol (7)), in anhydrous THF (500 mL), at −78° C. was added a 2.0 M solution of LDA in hexane (70 mL, 140 mmol) over a period of 30 min. The reaction was stirred at −78° C. for another 30 min. To the resulting white suspension isobutyraldehyde (8.4 mL, 116 mmol) was added drop-wise via syringe and the reaction continued for another 12 hrs at room temperature. The reaction was quenched by adding 10 mL of water. Approximately 80% THF was removed and the mixture was then poured into saturated aqueous solution of NH$_4$Cl. The aqueous layer was extracted twice with diethyl ether (200 mL) and the organic layer was washed with plenty of water. The organic layer was then dried over MgSO$_4$ and concentrated to give a crude white oil of (3-hydroxy ketone (16.5 g, 90%). The crude product was recrystallized from petroleum ether to give pure white solid (8) with a yield of 76%.

(3R,5S)-2,6-dimethylheptane-3,5-diol (DMH-Diol) (9): To a solution of (3-hydroxy ketone (10 g, 63 mmol, (8)) in THF (250 mL) was added 1 M DIBAL-H in hexane, (126 mL, 126 mmol) at −78° C., and the solution was stirred for 2 hrs at this temperature. The reaction mixture was allowed to warm to room temperature and continued for another 8 hrs at room temperature. After 8 hrs the reaction mixture was quenched with 2 N aqueous HCl solution. The mixture was then extracted twice with ether (200 mL), and the combined organic layer was washed with saturated aqueous NaHCO$_3$ solution and with brine. Drying with anhydrous MgSO$_4$ and concentration gave the crude DMH-Diol (8.5 g, 84% yield) as a white solid. The crude diol was further purified by column chromatography using petroleum ether and ethyl acetate mixture (80:20) to give purified product (9) with a yield of 72%.

Example 4

Preparation of pentadecane-7,9-diol (10)

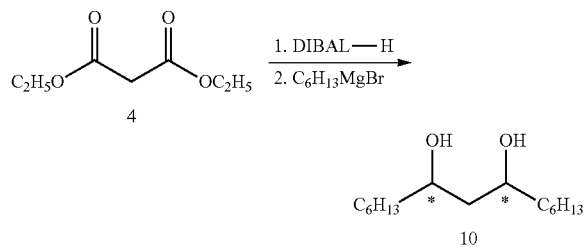

A solution of 1M DIBAL-H in toluene (125.0 mL, 125 mmol) was slowly added over a period of 10 mins, to a solution of diethylmalonate (10.0 mL, 62.5 mmol, (4)) in Et$_2$O (13.6 mL) at −78° C. under N$_2$. The internal temperature was maintained −78° C. The mixture was stirred for 1 h at −78° C. A solution of hexylmagnesium bromide in Et$_2$O (65.0 mL, 130 mmol) was added at −78° C. The reaction mixture was then warmed to room temperature and stirred for 6 h. The mixture was quenched with saturated NH$_4$Cl solution at 0° C. A saturated solution of Rochelle's salt was added at room temperature and the two-phase mixture was stirred for approximately 8 h. The aqueous layer was extracted with ethyl acetate. The combined organic layers were dried over Na$_2$SO$_4$. The solvent was removed in vacuum, and the resulting material was purified via column chromatography (30% Ethyacetate-70% hexanes) to provide the desired product (6.4 g, 42%, (10)).

Example 5

Preparation of 3,4-dimethoxyselenophene (DMOS) (12)

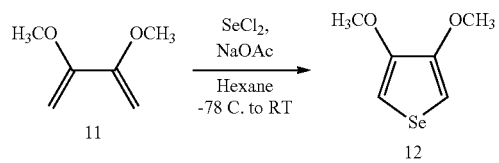

SeCl$_2$ was prepared by adding SO$_2$Cl$_2$ (2.0 g, 14.8 mmol) to selenium powder (1.18 g, 14.8 mmol) over a period of 5 min at 10-20° C. After 30 min, 10 mL hexane was added to it and the resulting reaction mixture was stirred for 4 h at room temperature. A clear brown solution of SeCl$_2$ was formed.

To a well stirred solution of 2,3-dimethoxy-1,3-butadiene (1.47 g, 12.9 mmol, (11)) and CH$_3$COONa (2.64 g, 32.25 mmol) in dry hexane (80 mL) at −78° C. (dry ice/acetone bath), under an inert atmosphere, was added a solution of freshly prepared SeCl$_2$ in hexane over a period of 15 min. The resulting yellowish solution was further stirred for 1 h at −78° C. and then removed from the cooling bath and the reaction mixture was brought to room temperature over a period of 2 h and further stirred for 5 h. The reaction mixture was filtered through neutral alumina and washed with hexane. The residue was concentrated to give brown yellow oil. The crude product was purified by flash column chromatography on TLC grade silica gel (Hexane:Ethyl acetate—95:5) to provide DMOS (0.85 g, 35%, (12)) as a white crystalline solid. mp. 43-45° C.

Example 6

Preparation of 2,2-Dihexyl(3,4-propylenedioxyselenophene)(ProDOS-Hex$_2$) (13)

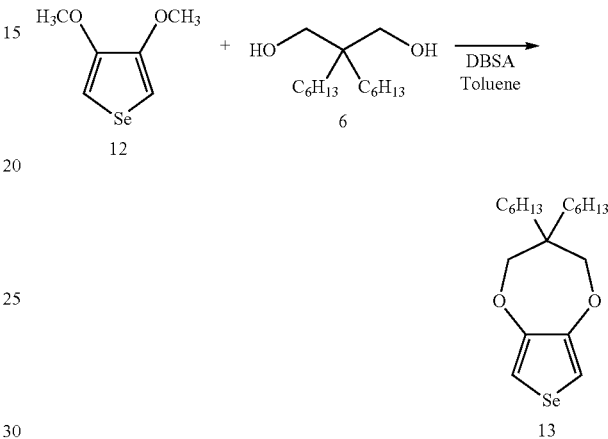

3,4-Dimethoxyselenophene (DMOS) (0.5 g, 2.60 mmol (12)), 2,2-dihexyl propane-1,3-diol (0.54 g, 5.20 mmol (6)), dodecylbenzene sulfonic acid (DBSA) (0.17 g, 0.52 mmol) and 100 mL of dry toluene were combined in a 3-neck round bottom flask equipped with a Soxhlet extractor with type 4 molecular sieves in the thimble. The solution was heated to reflux and allowed to reflux for 6 h. The reaction mixture was cooled, washed with dilute NaHCO3 solution and finally with water. Solid NaCl is used as an emulsion breaker. The toluene was removed under vacuum, and the crude product was purified by column chromatography on silica gel with 4:1 hexanes/ethylacetate as the eluent to yield ProDOS-Hex$_2$ (13) as a white solid (0.39 g, 65%). ProDOS-Hex$_2$ was characterized by using $^1$H-NMR, $^{13}$C-NMR, $^{77}$Se-NMR, GC-MS and GPC.

$^1$H-NMR (500 MHz, CDCl$_3$) δ 6.97 (s, 2H), 3.72 (s, 4H), 1.02 (s, 6H); $^{13}$C NMR: δ 151.44, 108.37, 80.05, 39.18, 21.98. $^{77}$Se NMR (400 MHz, CDCl$_3$) δ=394.9 ppm.

Example 7

Preparation of 2,2-Dimethyl(3,4-propylenedioxyselenophene) (ProDOS-Me$_2$) (15)

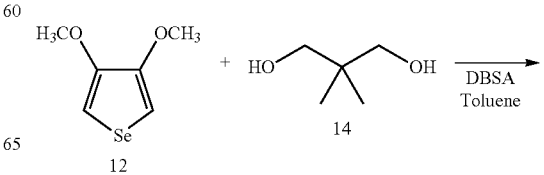

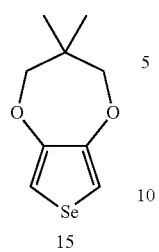

3,4-Dimethoxyselonophene (DMOS) (0.5 g, 2.60 mmol (12)), neopentyl glycol (0.54 g, 5.20 mmol (14)), dodecylbenzene sulfonic acid (DBSA) (0.17 g, 0.52 mmol) and 100 mL of dry toluene were combined in a 3-neck round bottom flask equipped with a Soxhlet extractor with type 4 A molecular sieves in the thimble the synthetic scheme is shown in the following scheme. The solution was heated to reflux and allowed to reflux for 12 hrs. The reaction mixture was cooled, washed with dilute NaHCO$_3$ solution and finally with water. Solid NaCl is used as an emulsion breaker. The toluene was removed under vacuum, and the crude product was purified by column chromatography on silica gel with 4:1 hexanes/ethylacetate as the eluent to yield Pro-DOS-Me$_2$ (15) as a white solid (0.39 g, 52%). ProDOS-Me$_2$ was characterized by using $^1$H-NMR, $^{13}$C-NMR, $^{77}$Se-NMR, GC-MS and GPC.

$^1$H-NMR (500 MHz, CDCl$_3$): δ 6.97 (s, 2H), 3.72 (s, 4H), 1.02 (s, 6H); $^{13}$C NMR: δ 151.44, 108.37, 80.05, 39.18, 21.98. $^{77}$Se NMR (400 MHz, CDCl$_3$) δ=394.9 ppm.

Example 8

Preparation of 3,4-dimethyl substituted 3,4-propylenedioxyselenophene (ProDOS-3,4-Me$_2$) (17)

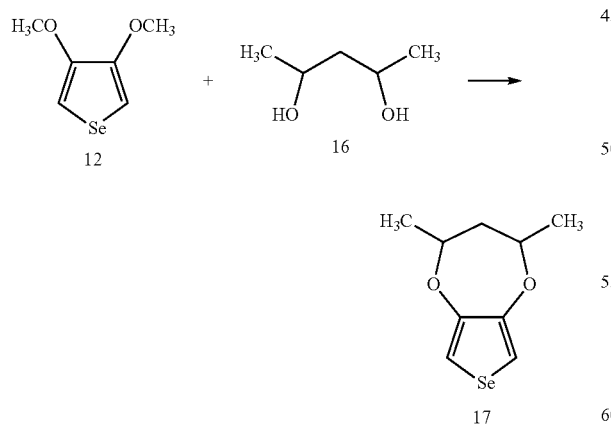

A transetherfication of 3,4-Dimethoxyselonophene (DMOS) (0.5 g, 2.60 mmol (12) with 2,4-pentanediol (16) in the presence of a catalytic amount of p-toluenesulfonic acid (p-TSA) or DBSA in toluene or xylene will produce ProDOS-3,4-Me$_2$ (17).

Example 9

Preparation of 3,4-ditert-butyl substituted 3,4-propylenedioxyselenophene (ProDOS-3,44-butyl$_2$) (18)

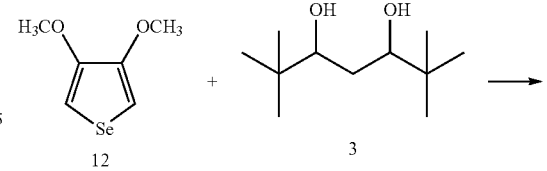

A transetherfication of 3,4-Dimethoxyselonophene (DMOS) (0.5 g, 2.60 mmol (12) with diol (3) in the presence of a catalytic amount of p-toluenesulfonic acid (p-TSA) or DBSA in toluene or xylene will produce ProDOS-3,44-butyl$_2$) (18).

Example 10

Preparation of 3,4-diisopropyl substituted 3,4-propylenedioxyselenophene (ProDOS-3,4-isopropyl$_2$) (19)

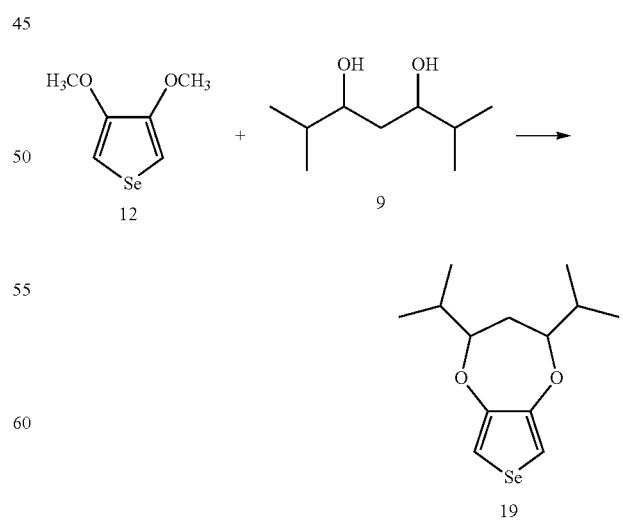

A transetherfication of 3,4-Dimethoxyselonophene (DMOS) (0.5 g, 2.60 mmol (12) with diol (9) in the presence of a catalytic amount of p-toluenesulfonic acid (p-TSA) or DBSA in toluene or xylene will produce ProDOS-3,4-isopropyl$_2$ (19).

Example 11

Preparation of 3,4-dihexyl substituted 3,4-propylenedioxyselenophene (ProDOS-3,4-hexyl$_2$) (20)

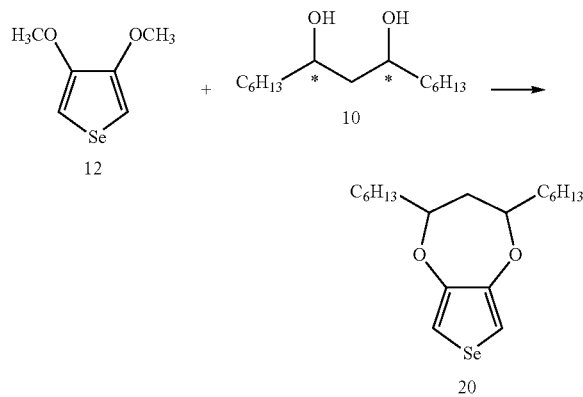

A transetherfication of 3,4-Dimethoxyselonophene (DMOS) (0.5 g, 2.60 mmol (12) with diol (10) in the presence of a catalytic amount of p-toluenesulfonic acid (p-TSA) or DBSA in toluene or xylene will produce ProDOS-3,4-hexyl$_2$ (20).

Example 12

Polymerization of DibromoProDOS-Hex$_2$

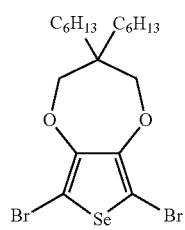

Chemical polymerization of DibromoProDOS-Hex$_2$ (21) was performed using FeCl$_3$ to form polyProDOS-Hex$_2$. PolyProDOS-Hex$_2$ is soluble in common organic solvents with a number average molecular weight of about 5800 g/mole. The soluble polymer obtained from ProDOS-Hex$_2$ was characterized by using $^1$H-NMR, $^{13}$C-NMR, $^{77}$Se-NMR, GC-MS and GPC.

Example 13

In-situ spectroelectrochemistry of PProDOS-Me$_2$ deposited onto ITO-coated-glass in 0.1 M TBAPF$_6$/ACN is illustrated in FIG. 1. Applied potential a) 0.6, b) 0.4 c) 0.2, d) 0.0, e) −0.1, f) −0.2, g) −0.3, h) −0.4, i) −0.5, j) −0.6 V vs non-aqueous Ag—Ag+ reference electrode (0.445 V vs NHE).

Example 14

Figure 2:
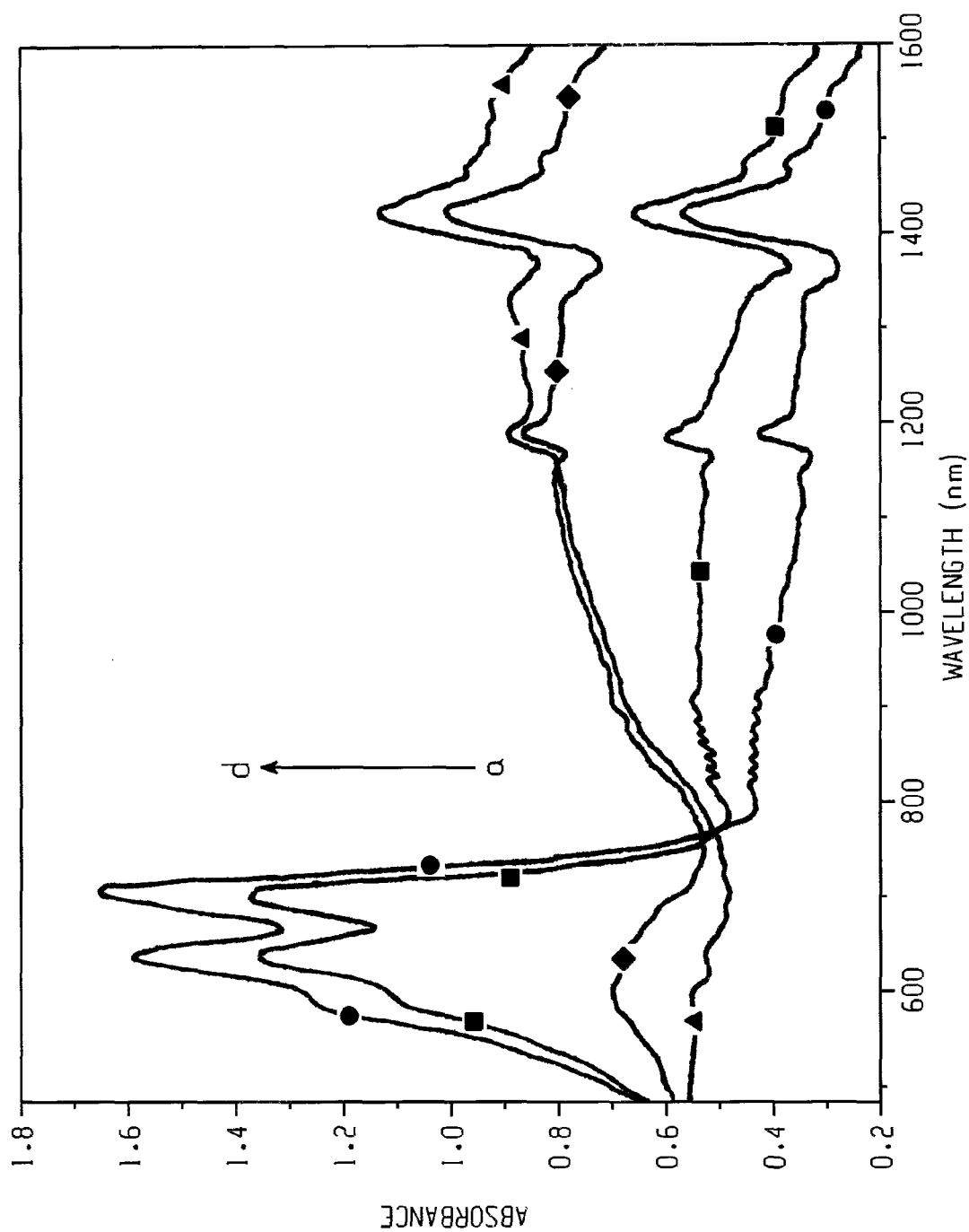
FIG. 2 is illustrates the in-situ spectroelectrochemistry of PProDOS-Hexyl$_2$ deposited onto ITO-coated-glass in 0.1 M TBAPF$_6$/ACN.

In-situ spectroelectrochemistry of PProDOS-Hexyl$_2$ deposited onto ITO-coated-glass in 0.1 M TBAPF$_6$/ACN is illustrated in FIG. 2. Applied potential of a) 0.6, b) 0.4 c) −0.4, d) −0.6 V vs non-aqueous Ag—Ag+ reference electrode (0.445 V vs NHE).

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including", and "containing" are to be construed as open-ended terms (i.e., meaning "including, but not limited to") unless otherwise noted. "Or" means and/or. Recitation of ranges of values herein are merely intended to serve as a shorthand method of referring individually to each separate value falling within the range, unless otherwise indicated herein, and each separate value is incorporated into the specification as if it were individually recited herein. All ranges disclosed herein are inclusive and combinable.

The essential characteristics of the present invention are described completely in the foregoing disclosure. One skilled in the art can understand the invention and make various modifications without departing from the basic spirit of the invention, and without deviating from the scope and equivalents of the claims, which follow. Moreover, any combination of the above-described elements in all possible variations thereof is encompassed by the invention unless otherwise indicated herein or otherwise clearly contradicted by context.

What is claimed is:
1. A compound, comprising:
a monomer according to any one of structure (I), (Ia), (II), and (IIa):

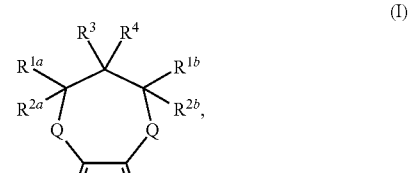

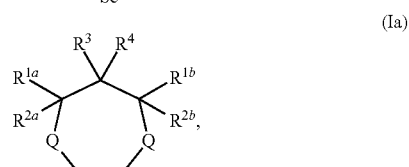

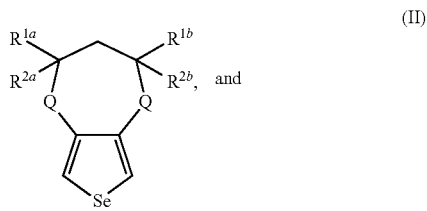

-continued

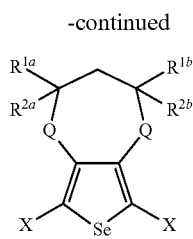
(IIa)

wherein each instance of Q is O or S;
X is chloro, bromo, or iodo;
each of $R^{1a}$, $R^{1b}$, $R^{2a}$, $R^{2b}$, $R^3$, and $R^4$ independently is hydrogen; $C_1$-$C_{20}$ alkyl, $C_1$-$C_{20}$ haloalkyl, aryl, $C_1$-$C_{20}$ alkoxy, $C_1$-$C_{20}$ haloalkoxy, aryloxy, —$C_1$-$C_{10}$ alkyl-O—$C_1$-$C_{10}$alkyl, —$C_1$-$C_{10}$alkyl-O-aryl, —$C_1$-$C_{10}$alkyl-aryl; or hydroxyl;
with the proviso that at least one of $R^{1a}$, $R^{1b}$, $R^{2a}$ $R^{2b}$, $R^3$, and $R^4$ is not hydrogen, and when $R^{1a}$, $R^{1b}$, $R^{2a}$, and $R^{2b}$ are all hydrogen, then at least one of $R^3$ and $R^4$ is other than hydrogen, $C_1$-$C_{20}$ alkyl, or —$C_1$-$C_{10}$ alkyl-aryl;
wherein the $C_1$-$C_{20}$ alkyl, $C_1$-$C_{20}$ haloalkyl, aryl, $C_1$-$C_{20}$ alkoxy, $C_1$-$C_{20}$ haloalkoxy, aryloxy, —$C_1$-$C_{10}$ alkyl-O—$C_1$-$C_{10}$ alkyl,—$C_1$-$C_{10}$ alkyl-O-aryl, —$C_1$-$C_{10}$ alkyl-aryl group each may be optionally substituted with one or more of $C_1$-$C_{20}$ alkyl; aryl; halogen; hydroxyl; —N—$(R^7)_2$ wherein each $R^7$ is independently hydrogen or $C_1$-$C_6$ alkyl; cyano; nitro; —COOH; —S(=O)$C_0$-$C_{10}$ alkyl; or —S(=O)$_2C_0$-$C_{10}$ alkyl.

2. The compound of claim 1, wherein both Q groups are O.
3. The compound of claim 1, wherein both Q groups are S.
4. The compound of claim 1, wherein each of $R^{1a}$, $R^{1b}$, $R^{2a}$ and $R^{2b}$ independently is hydrogen; optionally substituted $C_1$-$C_{10}$ alkyl, $C_1$-$C_{10}$ haloalkyl, aryl, $C_1$-$C_{10}$ alkoxy, $C_1$-$C_{10}$ haloalkoxy, aryloxy, —$C_1C_5$ alkyl-O—$C_1C_5$ alkyl, —$C_1$-$C_5$ alkyl-O-aryl, —$C_1$-$C_5$ alkyl-aryl; or hydroxyl; and $R^3$ and $R^4$ are both hydrogen, with the proviso that at least one of $R^{1a}$, $R^{1b}$, $R^{2a}$, and $R^{2b}$ is not hydrogen.
5. The compound of claim 1, wherein each of $R^{1a}$, $R^{1b}$, $R^{2a}$ and $R^{2b}$ independently is hydrogen; optionally substituted $C_1$-$C_5$ alkyl, $C_1$-$C_5$ haloalkyl, aryl, $C_1$-$C_5$ alkoxy, $C_1$-$C_5$ haloalkoxy, aryloxy, —$C_1$-$C_3$ alkyl-O—$C_1$-$C_3$ alkyl, —$C_1$-$C_3$ alkyl-O-aryl, —$C_1$-$C_3$ alkyl-aryl; or hydroxyl; and $R^3$ and $R^4$ are both hydrogen,
with the proviso that at least one of $R^{1a}$, $R^{1b}$, $R^{2a}$, and $R^{2b}$ is not hydrogen.
6. The compound of claim 1, wherein each of $R^{1a}$, $R^{1b}$, $R^{2a}$ and $R^{2b}$ independently is hydrogen; or optionally substituted $C_1$-$C_{20}$ alkyl, $C_1$-$C_{20}$ haloalkyl, aryl, —$C_1$-$C_{10}$ alkyl-aryl; and $R^3$ and $R^4$ are both hydrogen,
with the proviso that at least one of $R^{1a}$, $R^{1b}$, $R^{2a}$, and $R^{2b}$ is not hydrogen.
7. The compound of claim 1, wherein each of $R^{1a}$, $R^{1b}$, $R^{2a}$ and $R^{2b}$ independently is hydrogen; or optionally substituted $C_1$-$C_{20}$ alkyl, $C_1$-$C_{20}$ haloalkyl, aryl, —$C_1$-$C_{10}$ alkyl-aryl; and $R^3$ and $R^4$ are both hydrogen, with the proviso that at least two of $R^{1a}$, $R^{1b}$, $R^{2a}$ and $R^{2b}$ are not hydrogen.
8. The compound of claim 1, wherein at least two of and $R^{1a}$, $R^{1b}$, $R^{2a}$, and $R^{2b}$ are not hydrogen while the remaining two are hydrogen.
9. The compound of claim 1, wherein $R^{1a}$, $R^{1b}$, $R^{2a}$, and $R^{2b}$ are all hydrogen; $R^3$ and $R^4$ are each independently optionally substituted $C_3$-$C_{20}$ alkyl, $C_3$-$C_{20}$ haloalkyl, aryl, $C_3$-$C_{20}$ alkoxy, $C_3$-$C_{20}$ haloalkoxy, aryloxy, —$C_1$-$C_{10}$ alkyl-O—$C_1$-$C_{10}$ alkyl, —$C_1$-$C_{10}$ alkyl-O-aryl, —$C_3$-$C_{10}$ alkyl-aryl.
10. An article comprising the compound of any one of claims 1-9.

* * * * *